United States Patent
Friedel et al.

(10) Patent No.: US 7,772,349 B2
(45) Date of Patent: Aug. 10, 2010

(54) PROCESS FOR PREPARING ALKYLPOLYETHER-SUBSTITUTED MERCAPTOSILANES

(75) Inventors: Manuel Friedel, Zurich (CH); Susann Witzsche, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/127,931

(22) Filed: May 28, 2008

(65) Prior Publication Data

US 2009/0043066 A1 Feb. 12, 2009

(30) Foreign Application Priority Data

Aug. 9, 2007 (DE) .................. 10 2007 037 556

(51) Int. Cl.
*C08L 83/00* (2006.01)
(52) U.S. Cl. ....................................................... 528/10
(58) Field of Classification Search .................... 528/10
See application file for complete search history.

(56) References Cited

U.S. PATENT DOCUMENTS 6,489,500 B2 * 12/2002 Bowman et al. ............ 556/469

2004/0266968 A1  12/2004  Korth et al.
2006/0161015 A1 *  7/2006  Klockmann et al. ......... 556/427
2006/0252952 A1 * 11/2006  Korth et al. ................. 556/429

FOREIGN PATENT DOCUMENTS

| EP | 0 085 831 A2 | 8/1983 |
| EP | 1 683 801 A2 | 7/2006 |
| WO | WO 2008/009514 A1 | 1/2008 |

* cited by examiner

*Primary Examiner*—Ling-Siu Choi
*Assistant Examiner*—Chun-Cheng Wang
(74) *Attorney, Agent, or Firm*—Oblon, Spivak, McClelland, Maier & Neustadt, L.L.P.

(57) ABSTRACT

Process for preparing alkylpolyether-substituted mercaptosilanes of the general formula I, $$(X)_m(X')_n(X'')_o Si(-R^1-SR^2)_p \quad (I)$$

and a Hazen colour number of $\leq 250$ mg Pt—Co/L by reacting compounds of the general formula II, $$(X')_{m+n}(X'')_o Si(-R^1-SR^2)_p \quad (II)$$

with m equivalents of the compounds of the general formula III, $$H-O-((CR^3{}_2)_w-O-)_v Alk \quad (III)$$

using a proton-donating co-catalyst and, if desired, a further catalyst, and separating off liberated X'—H from the reaction mixture.

10 Claims, No Drawings

PROCESS FOR PREPARING ALKYLPOLYETHER-SUBSTITUTED MERCAPTOSILANES

BACKGROUND OF THE INVENTION

1. Field of the Invention

The present invention relates to a process for preparing alkylpolyether-substituted mercaptosilanes.

2. Description of the Background

The use of silanes as adhesion promoters is known. For instance, aminoalkyltrialkoxysilanes, methacryloyloxyalkyltrialkoxysilanes, polysulphanealkyltrialkoxysilanes and mercaptoalkyltrialkoxysilanes are used as promoters of adhesion between inorganic materials and organic polymers, as crosslinking agents and surface modifiers (E. P. Plueddemann, "Silane Coupling Agents", 2$^{nd}$ Ed., Plenum Press 1982, pages 1-53).

These adhesion promoters, or coupling agents or bonding agents, form bonds both to the filler and to the elastomer, and hence bring about effective interaction between the filler surface and the elastomer.

Moreover it is known that the use of commercially customary silane adhesion promoters having three alkoxy substituents on the silicon atom leads to the release of considerable amounts of alcohol during and after attachment to the filler (DE 22 55 577). Since it is usual to use trimethoxy-substituted and triethoxy-substituted silanes, the corresponding alcohols, methanol and ethanol, are released in considerable amounts (Berkemeier, D.; Hader, W.; Rinker, M.; Heiss, G., Mixing of silica compounds from the viewpoint of a manufacturer of internal mixers, Gummi, Fasern, Kunststoffe (2001), Volume 54(1), pages 17-22).

It is known, furthermore, that methoxy-substituted and ethoxy-substituted silanes are more reactive than the corresponding long-chain alkoxy-substituted silanes and are therefore able to attach more quickly to the filler, so that to date it has not been possible from a technical and economic viewpoint to do without the use of methoxy and ethoxy substituents (H. D. Luginsland, "A review on the chemistry and the reinforcement of the silica-silane filler system for rubber applications", Shaker Verlag Aachen 2002, page 25ff.).

Furthermore, DE 10137809, JP 62-181346, DE 3426987 and EP 0085831 disclose various mercaptosilanes. DE 102005032658.7 and EP 1285926 disclose alkyl-polyether-substituted mercaptosilanes which release less methanol and/or ethanol but have the same reactivity. These silanes can be synthesized by subjecting alkoxysilanes to catalysed reaction with an alkylpolyether alcohol.

A disadvantage of the known processes for the synthesis of alkylpolyether-substituted mercaptosilanes is the pale brown to orange-red colour which occurs, which may fluctuate depending on the quality and the preparation process of the mercaptosilane used.

U.S. Pat. No. 5,210,250 discloses a method of decolouring halogenated silanes by treatment with insoluble, cationic, surface-active substances.

A disadvantage of that method is that the decolouring takes place in a step downstream from the synthesis, which in operational practice entails a not inconsiderable level of extra cost and inconvenience.

Furthermore, EP 1188758 and EP 1153927 disclose methods of influencing the colour of bis(3-[triethoxysilyl]propyl) polysulphanes and -tetrasulphanes, respectively, by adding chloropropyltrichlorosilane during the sulphurization reaction. From US 20040092758 it is known that polysulphide silanes with a low level of coloration can be obtained by increasing the reaction temperature during the sulphurization reaction. Both methods intervene in the course of the reaction at a point at which polysulphide species of different chain lengths are present or are forming in the reaction mixture. In the customary processes of mercaptosilane preparation, as described in U.S. Pat. Nos. 6,680,398, 7,151,188, 5,840,952 or US 2005/0124822, polysulphide species of this kind ought not to form or ought to form to a far lesser extent.

It is an object of the present invention to provide a process for preparing alkylpolyether-substituted mercaptosilanes that yields the alkylpolyether-substituted mercaptosilanes with weaker coloration.

SUMMARY OF THE INVENTION

The invention provides a process for preparing alkylpolyether-substituted mercaptosilanes of the general formula I, $$(X)_m(X')_n(X'')_o Si(-R^1-SR^2)_p \tag{I}$$

where p is 1, 2 or 3; m is 1, 2 or 3; n and o are 0, 1 or 2; and m+p+n+o is 4, the groups X are alike or different and X is an alkylpolyether group $O-((CR^3{}_2)_w-O-)_v$Alk, where v=1-40, w=1-40, $R^3$ independently at each occurrence is H, a phenyl group or an unbranched or branched alkyl group, Alk is a branched or unbranched, saturated or unsaturated, substituted or unsubstituted, aliphatic, aromatic or mixed aliphatic/aromatic monovalent $C_1$-$C_{35}$, the groups X' are alike or different and X' is a branched or unbranched alkoxy group, a branched or unbranched $C_2$-$C_{25}$ alkenyloxy group, a $C_6$-$C_{35}$ aryloxy group, a branched or unbranched $C_7$-$C_{35}$ alkylaryloxy, a branched or unbranched $C_7$-$C_{35}$ aralkyloxy group, or a hydroxyl group (—OH), the groups X'' are alike or different and X'' independently at each occurrence is a branched or unbranched alkyl group, $R^1$ is a branched or unbranched, saturated or unsaturated, aliphatic, aromatic or mixed aliphatic/aromatic divalent $C_1$-$C_{30}$ hydrocarbon group which is unsubstituted or substituted by heteroatoms, $R^2$ is CN, H or —C(Het)-Alk, where Het is a doubly bonded heteroatom O, S or NAlk and Alk has the definition given above, having a Hazen colour number of ≦250 mg Pt—Co/L, preferably ≦200 mg Pt—Co/L, comprising reacting compounds of the general formula II, $$(X')_{m+n}(X'')_o Si(-R^1-SR^2)_p \tag{II}$$

where X', X'', $R^1$, $R^2$, m, n, o and p have the definitions given above, with m equivalents of the compounds of the general formula III, $$H-O-((CR^3{}_2)_w-O-)_v Alk \tag{III}$$

where $R^3$, Alk, v and w have the definitions given above, in the presence of a proton-donating co-catalyst and, optionally, a further catalyst, and separating off liberated X'—H from the reaction mixture.

DETAILED DESCRIPTION OF THE INVENTION

The invention provides a process for preparing alkylpolyether-substituted mercaptosilanes of the general formula I, $$(X)_m(X')_n(X'')_o Si(-R^1-SR^2)_p \tag{I}$$

where p is 1, 2 or 3, preferably 1; m is 1, 2 or 3; n and o are 0, 1 or 2; and m+p+n+o is 4, the groups X are alike or different and X is an alkylpolyether group O—((CR$^3{}_2$)$_w$—O—)$_v$Alk, preferably O—(CH$_2$—CH$_2$—O—)$_v$Alk or O—(CH(CH$_3$)—CH$_2$—O—)$_v$Alk, where v=1-40, preferably 2-30, more preferably 3-25, very preferably 4-20, most preferably 5-16, w=1-40, preferably 2-30, more preferably 2-20, very preferably 2-10, R$^3$ independently at each occurrence is H, a phenyl group or an unbranched or branched alkyl group, preferably a C$_1$-C$_{11}$ alkyl group, more preferably a CH$_3$ or CH$_2$—CH$_3$ group, Alk is a branched or unbranched, saturated or unsaturated, substituted or unsubstituted, aliphatic, aromatic or mixed aliphatic/aromatic monovalent C$_1$-C$_{35}$, preferably C$_2$-C$_{22}$, more preferably C$_3$-C$_{18}$, very preferably C$_4$-C$_{13}$, most preferably C$_6$-C$_{10}$, hydrocarbon group, the groups X' are alike or different and X' is a branched or unbranched alkoxy group, preferably C$_1$-C$_{18}$ alkoxy, more preferably —OCH$_3$, —OCH$_2$—CH$_3$, —OCH(CH$_3$)—CH$_3$, —OCH$_2$—CH$_2$—CH$_3$, —OC$_{12}$H$_{25}$, —OC$_{13}$H$_{27}$, —OC$_{14}$H$_{29}$ or C$_{15}$-C$_{18}$ alkoxy, a branched or unbranched C$_2$-C$_{25}$ alkenyloxy group, preferably C$_4$-C$_{20}$ alkenyloxy, more preferably C$_6$ to C$_{18}$ alkenyloxy, a C$_6$-C$_{35}$ aryloxy group, preferably C$_9$-C$_{30}$-aryloxy, more preferably phenyloxy (—OC$_6$H$_5$) or C$_9$-C$_{18}$ aryloxy, a branched or unbranched C$_7$-C$_{35}$ alkylaryloxy, preferably C$_9$-C$_{30}$ alkylaryloxy, more preferably benzyloxy (—O—CH$_2$—C$_6$H$_5$) or —O—CH$_2$—CH$_2$—C$_6$H$_5$, a branched or unbranched C$_7$-C$_{35}$ aralkyloxy group, preferably C$_9$-C$_{25}$ aralkyloxy, more preferably tolyloxy (—O—C$_6$H$_4$—CH$_3$) or a C$_9$-C$_{18}$ aralkyloxy group, or a hydroxyl group (—OH), the groups X" are alike or different and X" independently at each occurrence is a branched or unbranched alkyl group, preferably C$_1$-C$_{18}$ alkyl group, more preferably CH$_3$, CH$_2$—CH$_3$, CH(CH$_3$)—CH$_3$, CH$_2$—CH$_2$—CH$_3$ or C$_4$-C$_{18}$ alkyl group, R$^1$ is a branched or unbranched, saturated or unsaturated, aliphatic, aromatic or mixed aliphatic/aromatic divalent C$_1$-C$_{30}$ hydrocarbon group which is unsubstituted or substituted by heteroatoms, R$^2$ is CN, H or —C(Het)-Alk, where Het is a doubly bonded heteroatom O, S or NAlk and Alk has the definition given above, having a Hazen colour number of ≦250 mg Pt—Co/L, preferably ≦200 mg Pt—Co/L, comprising reacting compounds of the general formula II,

(X')$_{m+n}$(X")$_o$Si(—R$^1$—SR$^2$)$_p$     (II)

where X', X", R$^1$, R$^2$, m, n, o and p have the definitions given above, with m equivalents of the compounds of the general formula III,

H—O—((CR$^3{}_2$)$_w$—O—)$_v$Alk     (III)

where R$^3$, Alk, v and w have the definitions given above, in the presence of a proton-donating co-catalyst and, optionally, a further catalyst, and separating off liberated X'—H from the reaction mixture.

The liberated X'—H can be separated continuously or discontinuously from the reaction mixture.

The mercaptosilanes of the general formula I and II may be mixtures of different mercaptosilanes of the general formula I and II and/or may comprise their condensation products containing siloxane units.

Examples of preferred compounds of the general formula I with R$^2$=H include the following:

[(C$_{12}$H$_{25}$O—(CH$_2$—CH$_2$O)$_2$]Me$_2$Si(CH$_2$)$_3$SH,
[(C$_{12}$H$_{25}$O—(CH$_2$—CH$_2$O)$_3$]Me$_2$Si(CH$_2$)$_3$SH,
[(C$_{12}$H$_{25}$O—(CH$_2$—CH$_2$O)$_4$]Me$_2$Si(CH$_2$)$_3$SH,
[(C$_{12}$H$_{25}$O—(CH$_2$—CH$_2$O)$_5$]Me$_2$Si(CH$_2$)$_3$SH,
[(C$_{12}$H$_{25}$O—(CH$_2$—CH$_2$O)$_6$]Me$_2$Si(CH$_2$)$_3$SH,
[(C$_{13}$H$_{27}$O—(CH$_2$—CH$_2$O)$_2$]Me$_2$Si(CH$_2$)$_3$SH,
[(C$_{13}$H$_{27}$O—(CH$_2$—CH$_2$O)$_3$]Me$_2$Si(CH$_2$)$_3$SH,
[(C$_{13}$H$_{27}$O—(CH$_2$—CH$_2$O)$_4$]Me$_2$Si(CH$_2$)$_3$SH,
[(C$_{13}$H$_{27}$O—(CH$_2$—CH$_2$O)$_5$]Me$_2$Si(CH$_2$)$_3$SH,
[(C$_{13}$H$_{27}$O—(CH$_2$—CH$_2$O)$_6$]Me$_2$Si(CH$_2$)$_3$SH,
[(C$_{14}$H$_{29}$O—(CH$_2$—CH$_2$O)$_2$]Me$_2$Si(CH$_2$)$_3$SH,
[(C$_{14}$H$_{29}$O—(CH$_2$—CH$_2$O)$_3$]Me$_2$Si(CH$_2$)$_3$SH,
[(C$_{14}$H$_{29}$O—(CH$_2$—CH$_2$O)$_4$]Me$_2$Si(CH$_2$)$_3$SH,
[(C$_{14}$H$_{29}$O—(CH$_2$—CH$_2$O)$_5$]Me$_2$Si(CH$_2$)$_3$SH,
[(C$_{14}$H$_{29}$O—(CH$_2$—CH$_2$O)$_6$]Me$_2$Si(CH$_2$)$_3$SH,
[(C$_{15}$H$_{31}$O—(CH$_2$—CH$_2$O)$_2$]Me$_2$Si(CH$_2$)$_3$SH,
[(C$_{15}$H$_{31}$O—(CH$_2$—CH$_2$O)$_3$]Me$_2$Si(CH$_2$)$_3$SH,
[(C$_{15}$H$_{31}$O—(CH$_2$—CH$_2$O)$_4$]Me$_2$Si(CH$_2$)$_3$SH,
[(C$_{15}$H$_{31}$O—(CH$_2$—CH$_2$O)$_5$]Me$_2$Si(CH$_2$)$_3$SH,
[(C$_{15}$H$_{31}$O—(CH$_2$—CH$_2$O)$_6$]Me$_2$Si(CH$_2$)$_3$SH,
[(C$_{16}$H$_{33}$O—(CH$_2$—CH$_2$O)$_2$]Me$_2$Si(CH$_2$)$_3$SH,
[(C$_{16}$H$_{33}$O—(CH$_2$—CH$_2$O)$_3$]Me$_2$Si(CH$_2$)$_3$SH,
[(C$_{16}$H$_{33}$O—(CH$_2$—CH$_2$O)$_4$]Me$_2$Si(CH$_2$)$_3$SH,
[(C$_{16}$H$_{33}$O—(CH$_2$—CH$_2$O)$_5$]Me$_2$Si(CH$_2$)$_3$SH,
[(C$_{16}$H$_{33}$O—(CH$_2$—CH$_2$O)$_6$]Me$_2$Si(CH$_2$)$_3$SH,
[(C$_{12}$H$_{25}$O—(CH$_2$—CH$_2$O)$_2$]$_2$MeSi(CH$_2$)$_3$SH,
[(C$_{12}$H$_{25}$O—(CH$_2$—CH$_2$O)$_3$]$_2$MeSi(CH$_2$)$_3$SH,
[(C$_{12}$H$_{25}$O—(CH$_2$—CH$_2$O)$_4$]$_2$MeSi(CH$_2$)$_3$SH,
[(C$_{12}$H$_{25}$O—(CH$_2$—CH$_2$O)$_5$]$_2$MeSi(CH$_2$)$_3$SH,
[(C$_{12}$H$_{25}$O—(CH$_2$—CH$_2$O)$_6$]$_2$MeSi(CH$_2$)$_3$SH,
[(C$_{13}$H$_{27}$O—(CH$_2$—CH$_2$O)$_2$]$_2$MeSi(CH$_2$)$_3$SH,
[(C$_{13}$H$_{27}$O—(CH$_2$—CH$_2$O)$_3$]$_2$MeSi(CH$_2$)$_3$SH,
[(C$_{13}$H$_{27}$O—(CH$_2$—CH$_2$O)$_4$]$_2$MeSi(CH$_2$)$_3$SH,
[(C$_{13}$H$_{27}$O—(CH$_2$—CH$_2$O)$_5$]$_2$MeSi(CH$_2$)$_3$SH,
[(C$_{13}$H$_{27}$O—(CH$_2$—CH$_2$O)$_6$]$_2$MeSi(CH$_2$)$_3$SH,
[(C$_{14}$H$_{29}$O—(CH$_2$—CH$_2$O)$_2$]$_2$MeSi(CH$_2$)$_3$SH,
[(C$_{14}$H$_{29}$O—(CH$_2$—CH$_2$O)$_3$]$_2$MeSi(CH$_2$)$_3$SH,
[(C$_{14}$H$_{29}$O—(CH$_2$—CH$_2$O)$_4$]$_2$MeSi(CH$_2$)$_3$SH,
[(C$_{14}$H$_{29}$O—(CH$_2$—CH$_2$O)$_5$]$_2$MeSi(CH$_2$)$_3$SH,
[(C$_{14}$H$_{29}$O—(CH$_2$—CH$_2$O)$_6$]$_2$MeSi(CH$_2$)$_3$SH,
[(C$_{15}$H$_{31}$O—(CH$_2$—CH$_2$O)$_2$]$_2$MeSi(CH$_2$)$_3$SH,
[(C$_{15}$H$_{31}$O—(CH$_2$—CH$_2$O)$_3$]$_2$MeSi(CH$_2$)$_3$SH,
[(C$_{15}$H$_{31}$O—(CH$_2$—CH$_2$O)$_4$]$_2$MeSi(CH$_2$)$_3$SH,
[(C$_{15}$H$_{31}$O—(CH$_2$—CH$_2$O)$_5$]$_2$MeSi(CH$_2$)$_3$SH,
[(C$_{15}$H$_{31}$O—(CH$_2$—CH$_2$O)$_6$]$_2$MeSi(CH$_2$)$_3$SH,
[(C$_{16}$H$_{33}$O—(CH$_2$—CH$_2$O)$_2$]$_2$MeSi(CH$_2$)$_3$SH,
[(C$_{16}$H$_{33}$O—(CH$_2$—CH$_2$O)$_3$]$_2$MeSi(CH$_2$)$_3$SH,
[(C$_{16}$H$_{33}$O—(CH$_2$—CH$_2$O)$_4$]$_2$MeSi(CH$_2$)$_3$SH,
[(C$_{16}$H$_{33}$O—(CH$_2$—CH$_2$O)$_5$]$_2$MeSi(CH$_2$)$_3$SH,
[(C$_{16}$H$_{33}$O—(CH$_2$—CH$_2$O)$_6$]$_2$MeSi(CH$_2$)$_3$SH,
[(C$_{11}$H$_{23}$O—(CH$_2$—CH$_2$O)$_2$](MeO)$_2$Si(CH$_2$)$_3$SH,
[(C$_{11}$H$_{23}$O—(CH$_2$—CH$_2$O)$_3$](MeO)$_2$Si(CH$_2$)$_3$SH,
[(C$_{11}$H$_{23}$O—(CH$_2$—CH$_2$O)$_4$](MeO)$_2$Si(CH$_2$)$_3$SH,
[(C$_{11}$H$_{23}$O—(CH$_2$—CH$_2$O)$_5$](MeO)$_2$Si(CH$_2$)$_3$SH,
[(C$_{11}$H$_{23}$O—(CH$_2$—CH$_2$O)$_6$](MeO)$_2$Si(CH$_2$)$_3$SH,
[(C$_{12}$H$_{25}$O—(CH$_2$—CH$_2$O)$_2$](MeO)$_2$Si(CH$_2$)$_3$SH,
[(C$_{12}$H$_{25}$O—(CH$_2$—CH$_2$O)$_3$](MeO)$_2$Si(CH$_2$)$_3$SH,
[(C$_{12}$H$_{25}$O—(CH$_2$—CH$_2$O)$_4$](MeO)$_2$Si(CH$_2$)$_3$SH,
[(C$_{12}$H$_{25}$O—(CH$_2$—CH$_2$O)$_5$](MeO)$_2$Si(CH$_2$)$_3$SH,
[(C$_{12}$H$_{25}$O—(CH$_2$—CH$_2$O)$_6$](MeO)$_2$Si(CH$_2$)$_3$SH,
[(C$_{13}$H$_{27}$O—(CH$_2$—CH$_2$O)$_2$](MeO)$_2$Si(CH$_2$)$_3$SH,

[(C₁₃H₂₇O—(CH₂—CH₂O)₃](MeO)₂Si(CH₂)₃SH,
[(C₁₃H₂₇O—(CH₂—CH₂O)₄](MeO)₂Si(CH₂)₃SH,
[(C₁₃H₂₇O—(CH₂—CH₂O)₅](MeO)₂Si(CH₂)₃SH,
[(C₁₃H₂₇O—(CH₂—CH₂O)₆](MeO)₂Si(CH₂)₃SH,
[(C₁₄H₂₉O—(CH₂—CH₂O)₂](MeO)₂Si(CH₂)₃SH,
[(C₁₄H₂₉O—(CH₂—CH₂O)₃](MeO)₂Si(CH₂)₃SH,
[(C₁₄H₂₉O—(CH₂—CH₂O)₄](MeO)₂Si(CH₂)₃SH,
[(C₁₄H₂₉O—(CH₂—CH₂O)₅](MeO)₂Si(CH₂)₃SH,
[(C₁₄H₂₉O—(CH₂—CH₂O)₆](MeO)₂Si(CH₂)₃SH,
[(C₁₅H₃₁O—(CH₂—CH₂O)₂](MeO)₂Si(CH₂)₃SH,
[(C₁₅H₃₁O—(CH₂—CH₂O)₃](MeO)₂Si(CH₂)₃SH,
[(C₁₅H₃₁O—(CH₂—CH₂O)₄](MeO)₂Si(CH₂)₃SH,
[(C₁₅H₃₁O—(CH₂—CH₂O)₅](MeO)₂Si(CH₂)₃SH,
[(C₁₅H₃₁O—(CH₂—CH₂O)₆](MeO)₂Si(CH₂)₃SH,
[(C₁₆H₃₃O—(CH₂—CH₂O)₂](MeO)₂Si(CH₂)₃SH,
[(C₁₆H₃₃O—(CH₂—CH₂O)₃](MeO)₂Si(CH₂)₃SH,
[(C₁₆H₃₃O—(CH₂—CH₂O)₄](MeO)₂Si(CH₂)₃SH,
[(C₁₆H₃₃O—(CH₂—CH₂O)₅](MeO)₂Si(CH₂)₃SH,
[(C₁₆H₃₃O—(CH₂—CH₂O)₆](MeO)₂Si(CH₂)₃SH,
[(C₁₇H₃₅O—(CH₂—CH₂O)₂](MeO)₂Si(CH₂)₃SH,
[(C₁₇H₃₅O—(CH₂—CH₂O)₃](MeO)₂Si(CH₂)₃SH,
[(C₁₇H₃₅O—(CH₂—CH₂O)₄](MeO)₂Si(CH₂)₃SH,
[(C₁₇H₃₅O—(CH₂—CH₂O)₅](MeO)₂Si(CH₂)₃SH,
[(C₁₇H₃₅O—(CH₂—CH₂O)₆](MeO)₂Si(CH₂)₃SH,
[(C₁₁H₂₃O—(CH₂—CH₂O)₂]₂(MeO)Si(CH₂)₃SH,
[(C₁₁H₂₃O—(CH₂—CH₂O)₃]₂(MeO)Si(CH₂)₃SH,
[(C₁₁H₂₃O—(CH₂—CH₂O)₄]₂(MeO)Si(CH₂)₃SH,
[(C₁₁H₂₃O—(CH₂—CH₂O)₅]₂(MeO)Si(CH₂)₃SH,
[(C₁₁H₂₃O—(CH₂—CH₂O)₆]₂(MeO)Si(CH₂)₃SH,
[(C₁₂H₂₅O—(CH₂—CH₂O)₂]₂(MeO)Si(CH₂)₃SH,
[(C₁₂H₂₅O—(CH₂—CH₂O)₃]₂(MeO)Si(CH₂)₃SH,
[(C₁₂H₂₅O—(CH₂—CH₂O)₄]₂(MeO)Si(CH₂)₃SH,
[(C₁₂H₂₅O—(CH₂—CH₂O)₅]₂(MeO)Si(CH₂)₃SH,
[(C₁₂H₂₅O—(CH₂—CH₂O)₆]₂(MeO)Si(CH₂)₃SH,
[(C₁₃H₂₇O—(CH₂—CH₂O)₂]₂(MeO)Si(CH₂)₃SH,
[(C₁₃H₂₇O—(CH₂—CH₂O)₃]₂(MeO)Si(CH₂)₃SH,
[(C₁₃H₂₇O—(CH₂—CH₂O)₄]₂(MeO)Si(CH₂)₃SH,
[(C₁₃H₂₇O—(CH₂—CH₂O)₅]₂(MeO)Si(CH₂)₃SH,
[(C₁₃H₂₇O—(CH₂—CH₂O)₆]₂(MeO)Si(CH₂)₃SH,
[(C₁₄H₂₉O—(CH₂—CH₂O)₂]₂(MeO)Si(CH₂)₃SH,
[(C₁₄H₂₉O—(CH₂—CH₂O)₃]₂(MeO)Si(CH₂)₃SH,
[(C₁₄H₂₉O—(CH₂—CH₂O)₄]₂(MeO)Si(CH₂)₃SH,
[(C₁₄H₂₉O—(CH₂—CH₂O)₅]₂(MeO)Si(CH₂)₃SH,
[(C₁₄H₂₉O—(CH₂—CH₂O)₆]₂(MeO)Si(CH₂)₃SH,
[(C₁₅H₃₁O—(CH₂—CH₂O)₂]₂(MeO)Si(CH₂)₃SH,
[(C₁₅H₃₁O—(CH₂—CH₂O)₃]₂(MeO)Si(CH₂)₃SH,
[(C₁₅H₃₁O—(CH₂—CH₂O)₄]₂(MeO)Si(CH₂)₃SH,
[(C₁₅H₃₁O—(CH₂—CH₂O)₅]₂(MeO)Si(CH₂)₃SH,
[(C₁₅H₃₁O—(CH₂—CH₂O)₆]₂(MeO)Si(CH₂)₃SH,
[(C₁₆H₃₃O—(CH₂—CH₂O)₂]₂(MeO)Si(CH₂)₃SH,
[(C₁₆H₃₃O—(CH₂—CH₂O)₃]₂(MeO)Si(CH₂)₃SH,
[(C₁₆H₃₃O—(CH₂—CH₂O)₄]₂(MeO)Si(CH₂)₃SH,
[(C₁₆H₃₃O—(CH₂—CH₂O)₅]₂(MeO)Si(CH₂)₃SH,
[(C₁₆H₃₃O—(CH₂—CH₂O)₆]₂(MeO)Si(CH₂)₃SH,
[(C₁₇H₃₅O—(CH₂—CH₂O)₂]₂(MeO)Si(CH₂)₃SH,
[(C₁₇H₃₅O—(CH₂—CH₂O)₃]₂(MeO)Si(CH₂)₃SH,
[(C₁₇H₃₅O—(CH₂—CH₂O)₄]₂(MeO)Si(CH₂)₃SH,
[(C₁₇H₃₅O—(CH₂—CH₂O)₅]₂(MeO)Si(CH₂)₃SH,
[(C₁₇H₃₅O—(CH₂—CH₂O)₆]₂(MeO)Si(CH₂)₃SH,
[(C₁₁H₂₃O—(CH₂—CH₂O)₂](EtO)₂Si(CH₂)₃SH,
[(C₁₁H₂₃O—(CH₂—CH₂O)₃](EtO)₂Si(CH₂)₃SH,
[(C₁₁H₂₃O—(CH₂—CH₂O)₄](EtO)₂Si(CH₂)₃SH,
[(C₁₁H₂₃O—(CH₂—CH₂O)₅](EtO)₂Si(CH₂)₃SH,
[(C₁₁H₂₃O—(CH₂—CH₂O)₆](EtO)₂Si(CH₂)₃SH,
[(C₁₂H₂₅O—(CH₂—CH₂O)₂](EtO)₂Si(CH₂)₃SH,
[(C₁₂H₂₅O—(CH₂—CH₂O)₃](EtO)₂Si(CH₂)₃SH,
[(C₁₂H₂₅O—(CH₂—CH₂O)₄](EtO)₂Si(CH₂)₃SH,
[(C₁₂H₂₅O—(CH₂—CH₂O)₅](EtO)₂Si(CH₂)₃SH,
[(C₁₂H₂₅O—(CH₂—CH₂O)₆](EtO)₂Si(CH₂)₃SH,
[(C₁₃H₂₇O—(CH₂—CH₂O)₂](EtO)₂Si(CH₂)₃SH,
[(C₁₃H₂₇O—(CH₂—CH₂O)₃](EtO)₂Si(CH₂)₃SH,
[(C₁₃H₂₇O—(CH₂—CH₂O)₄](EtO)₂Si(CH₂)₃SH,
[(C₁₃H₂₇O—(CH₂—CH₂O)₅](EtO)₂Si(CH₂)₃SH,
[(C₁₃H₂₇O—(CH₂—CH₂O)₆](EtO)₂Si(CH₂)₃SH,
[(C₁₄H₂₉O—(CH₂—CH₂O)₂](EtO)₂Si(CH₂)₃SH,
[(C₁₄H₂₉O—(CH₂—CH₂O)₃](EtO)₂Si(CH₂)₃SH,
[(C₁₄H₂₉O—(CH₂—CH₂O)₄](EtO)₂Si(CH₂)₃SH,
[(C₁₄H₂₉O—(CH₂—CH₂O)₅](EtO)₂Si(CH₂)₃SH,
[(C₁₄H₂₉O—(CH₂—CH₂O)₆](EtO)₂Si(CH₂)₃SH,
[(C₁₅H₃₁O—(CH₂—CH₂O)₂](EtO)₂Si(CH₂)₃SH,
[(C₁₅H₃₁O—(CH₂—CH₂O)₃](EtO)₂Si(CH₂)₃SH,
[(C₁₅H₃₁O—(CH₂—CH₂O)₄](EtO)₂Si(CH₂)₃SH,
[(C₁₅H₃₁O—(CH₂—CH₂O)₅](EtO)₂Si(CH₂)₃SH,
[(C₁₅H₃₁O—(CH₂—CH₂O)₆](EtO)₂Si(CH₂)₃SH,
[(C₁₆H₃₃O—(CH₂—CH₂O)₂](EtO)₂Si(CH₂)₃SH,
[(C₁₆H₃₃O—(CH₂—CH₂O)₃](EtO)₂Si(CH₂)₃SH,
[(C₁₆H₃₃O—(CH₂—CH₂O)₄](EtO)₂Si(CH₂)₃SH,
[(C₁₆H₃₃O—(CH₂—CH₂O)₅](EtO)₂Si(CH₂)₃SH,
[(C₁₆H₃₃O—(CH₂—CH₂O)₆](EtO)₂Si(CH₂)₃SH,
[(C₁₇H₃₅O—(CH₂—CH₂O)₂](EtO)₂Si(CH₂)₃SH,
[(C₁₇H₃₅O—(CH₂—CH₂O)₃](EtO)₂Si(CH₂)₃SH,
[(C₁₇H₃₅O—(CH₂—CH₂O)₄](EtO)₂Si(CH₂)₃SH,
[(C₁₇H₃₅O—(CH₂—CH₂O)₅](EtO)₂Si(CH₂)₃SH,
[(C₁₇H₃₅O—(CH₂—CH₂O)₆](EtO)₂Si(CH₂)₃SH,
[(C₁₁H₂₃O—(CH₂—CH₂O)₂]₂(EtO)Si(CH₂)₃SH,
[(C₁₁H₂₃O—(CH₂—CH₂O)₃]₂(EtO)Si(CH₂)₃SH,
[(C₁₁H₂₃O—(CH₂—CH₂O)₄]₂(EtO)Si(CH₂)₃SH,
[(C₁₁H₂₃O—(CH₂—CH₂O)₅]₂(EtO)Si(CH₂)₃SH,
[(C₁₁H₂₃O—(CH₂—CH₂O)₆]₂(EtO)Si(CH₂)₃SH,
[(C₁₂H₂₅O—(CH₂—CH₂O)₂]₂(EtO)Si(CH₂)₃SH,
[(C₁₂H₂₅O—(CH₂—CH₂O)₃]₂(EtO)Si(CH₂)₃SH,
[(C₁₂H₂₅O—(CH₂—CH₂O)₄]₂(EtO)Si(CH₂)₃SH,
[(C₁₂H₂₅O—(CH₂—CH₂O)₅]₂(EtO)Si(CH₂)₃SH,
[(C₁₂H₂₅O—(CH₂—CH₂O)₆]₂(EtO)Si(CH₂)₃SH,
[(C₁₃H₂₇O—(CH₂—CH₂O)₂]₂(EtO)Si(CH₂)₃SH,
[(C₁₃H₂₇O—(CH₂—CH₂O)₃]₂(EtO)Si(CH₂)₃SH,
[(C₁₃H₂₇O—(CH₂—CH₂O)₄]₂(EtO)Si(CH₂)₃SH,
[(C₁₃H₂₇O—(CH₂—CH₂O)₅]₂(EtO)Si(CH₂)₃SH,
[(C₁₃H₂₇O—(CH₂—CH₂O)₆]₂(EtO)Si(CH₂)₃SH,
[(C₁₄H₂₉O—(CH₂—CH₂O)₂]₂(EtO)Si(CH₂)₃SH,
[(C₁₄H₂₉O—(CH₂—CH₂O)₃]₂(EtO)Si(CH₂)₃SH,
[(C₁₄H₂₉O—(CH₂—CH₂O)₄]₂(EtO)Si(CH₂)₃SH,
[(C₁₄H₂₉O—(CH₂—CH₂O)₅]₂(EtO)Si(CH₂)₃SH,
[(C₁₄H₂₉O—(CH₂—CH₂O)₆]₂(EtO)Si(CH₂)₃SH,
[(C₁₅H₃₁O—(CH₂—CH₂O)₂]₂(EtO)Si(CH₂)₃SH,
[(C₁₅H₃₁O—(CH₂—CH₂O)₃]₂(EtO)Si(CH₂)₃SH,
[(C₁₅H₃₁O—(CH₂—CH₂O)₄]₂(EtO)Si(CH₂)₃SH,
[(C₁₅H₃₁O—(CH₂—CH₂O)₅]₂(EtO)Si(CH₂)₃SH,
[(C₁₅H₃₁O—(CH₂—CH₂O)₆]₂(EtO)Si(CH₂)₃SH,
[(C₁₆H₃₃O—(CH₂—CH₂O)₂]₂(EtO)Si(CH₂)₃SH,
[(C₁₆H₃₃O—(CH₂—CH₂O)₃]₂(EtO)Si(CH₂)₃SH,
[(C₁₆H₃₃O—(CH₂—CH₂O)₄]₂(EtO)Si(CH₂)₃SH,
[(C₁₆H₃₃O—(CH₂—CH₂O)₅]₂(EtO)Si(CH₂)₃SH,
[(C₁₆H₃₃O—(CH₂—CH₂O)₆]₂(EtO)Si(CH₂)₃SH,
[(C₁₇H₃₅O—(CH₂—CH₂O)₂]₂(EtO)Si(CH₂)₃SH,
[(C₁₇H₃₅O—(CH₂—CH₂O)₃]₂(EtO)Si(CH₂)₃SH,
[(C₁₇H₃₅O—(CH₂—CH₂O)₄]₂(EtO)Si(CH₂)₃SH,
[(C₁₇H₃₅O—(CH₂—CH₂O)₅]₂(EtO)Si(CH₂)₃SH,
[(C₁₇H₃₅O—(CH₂—CH₂O)₆]₂(EtO)Si(CH₂)₃SH,
[(C₁₁H₂₃O—(CH₂—CH₂O)₂]₂(HO)Si(CH₂)₃SH,
[(C₁₁H₂₃O—(CH₂—CH₂O)₃]₂(HO)Si(CH₂)₃SH,
[(C₁₁H₂₃O—(CH₂—CH₂O)₄]₂(HO)Si(CH₂)₃SH,
[(C₁₁H₂₃O—(CH₂—CH₂O)₅]₂(HO)Si(CH₂)₃SH,
[(C₁₁H₂₃O—(CH₂—CH₂O)₆]₂(HO)Si(CH₂)₃SH,

[(C₁₂H₂₅O—(CH₂—CH₂O)₂]₂(HO)Si(CH₂)₃SH,
[(C₁₂H₂₅O—(CH₂—CH₂O)₃]₂(HO)Si(CH₂)₃SH,
[(C₁₂H₂₅O—(CH₂—CH₂O)₄]₂(HO)Si(CH₂)₃SH,
[(C₁₂H₂₅O—(CH₂—CH₂O)₅]₂(HO)Si(CH₂)₃SH,
[(C₁₂H₂₅O—(CH₂—CH₂O)₆]₂(HO)Si(CH₂)₃SH,
[(C₁₃H₂₇O—(CH₂—CH₂O)₂]₂(HO)Si(CH₂)₃SH,
[(C₁₃H₂₇O—(CH₂—CH₂O)₃]₂(HO)Si(CH₂)₃SH,
[(C₁₃H₂₇O—(CH₂—CH₂O)₄]₂(HO)Si(CH₂)₃SH,
[(C₁₃H₂₇O—(CH₂—CH₂O)₅]₂(HO)Si(CH₂)₃SH,
[(C₁₃H₂₇O—(CH₂—CH₂O)₆]₂(HO)Si(CH₂)₃SH,
[(C₁₄H₂₉O—(CH₂—CH₂O)₂]₂(HO)Si(CH₂)₃SH,
[(C₁₄H₂₉O—(CH₂—CH₂O)₃]₂(HO)Si(CH₂)₃SH,
[(C₁₄H₂₉O—(CH₂—CH₂O)₄]₂(HO)Si(CH₂)₃SH,
[(C₁₄H₂₉O—(CH₂—CH₂O)₅]₂(HO)Si(CH₂)₃SH,
[(C₁₄H₂₉O—(CH₂—CH₂O)₆]₂(HO)Si(CH₂)₃SH,
[(C₁₅H₃₁O—(CH₂—CH₂O)₂]₂(HO)Si(CH₂)₃SH,
[(C₁₅H₃₁O—(CH₂—CH₂O)₃]₂(HO)Si(CH₂)₃SH,
[(C₁₅H₃₁O—(CH₂—CH₂O)₄]₂(HO)Si(CH₂)₃SH,
[(C₁₅H₃₁O—(CH₂—CH₂O)₅]₂(HO)Si(CH₂)₃SH,
[(C₁₅H₃₁O—(CH₂—CH₂O)₆]₂(HO)Si(CH₂)₃SH,
[(C₁₆H₃₃O—(CH₂—CH₂O)₂]₂(HO)Si(CH₂)₃SH,
[(C₁₆H₃₃O—(CH₂—CH₂O)₃]₂(HO)Si(CH₂)₃SH,
[(C₁₆H₃₃O—(CH₂—CH₂O)₄]₂(EtO)Si(CH₂)₃SH,
[(C₁₆H₃₃O—(CH₂—CH₂O)₅]₂(HO)Si(CH₂)₃SH,
[(C₁₆H₃₃O—(CH₂—CH₂O)₆]₂(HO)Si(CH₂)₃SH,
[(C₁₇H₃₅O—(CH₂—CH₂O)₂]₂(HO)Si(CH₂)₃SH,
[(C₁₇H₃₅O—(CH₂—CH₂O)₃]₂(HO)Si(CH₂)₃SH,
[(C₁₇H₃₅O—(CH₂—CH₂O)₄]₂(HO)Si(CH₂)₃SH,
[(C₁₇H₃₅O—(CH₂—CH₂O)₅]₂(HO)Si(CH₂)₃SH,
[(C₁₇H₃₅O—(CH₂—CH₂O)₆]₂(HO)Si(CH₂)₃SH,
[(C₁₁H₂₃O—(CH₂—CH₂O)₂]₃Si(CH₂)₃SH,
[(C₁₁H₂₃O—(CH₂—CH₂O)₃]₃Si(CH₂)₃SH,
[(C₁₁H₂₃O—(CH₂—CH₂O)₄]₃Si(CH₂)₃SH,
[(C₁₁H₂₃O—(CH₂—CH₂O)₅]₃Si(CH₂)₃SH,
[(C₁₁H₂₃O—(CH₂—CH₂O)₆]₃Si(CH₂)₃SH,
[(C₁₂H₂₅O—(CH₂—CH₂O)₂]₃Si(CH₂)₃SH,
[(C₁₂H₂₅O—(CH₂—CH₂O)₃]₃Si(CH₂)₃SH,
[(C₁₂H₂₅O—(CH₂—CH₂O)₄]₃Si(CH₂)₃SH,
[(C₁₂H₂₅O—(CH₂—CH₂O)₅]₃Si(CH₂)₃SH,
[(C₁₂H₂₅O—(CH₂—CH₂O)₆]₃Si(CH₂)₃SH,
[(C₁₃H₂₇O—(CH₂—CH₂O)₂]₃Si(CH₂)₃SH,
[(C₁₃H₂₇O—(CH₂—CH₂O)₃]₃Si(CH₂)₃SH,
[(C₁₃H₂₇O—(CH₂—CH₂O)₄]₃Si(CH₂)₃SH,
[(C₁₃H₂₇O—(CH₂—CH₂O)₅]₃Si(CH₂)₃SH,
[(C₁₃H₂₇O—(CH₂—CH₂O)₆]₃Si(CH₂)₃SH,
[(C₁₄H₂₉O—(CH₂—CH₂O)₂]₃Si(CH₂)₃SH,
[(C₁₄H₂₉O—(CH₂—CH₂O)₃]₃Si(CH₂)₃SH,
[(C₁₄H₂₉O—(CH₂—CH₂O)₄]₃Si(CH₂)₃SH,
[(C₁₄H₂₉O—(CH₂—CH₂O)₅]₃Si(CH₂)₃SH,
[(C₁₄H₂₉O—(CH₂—CH₂O)₆]₃Si(CH₂)₃SH,
[(C₁₅H₃₁O—(CH₂—CH₂O)₂]₃Si(CH₂)₃SH,
[(C₁₅H₃₁O—(CH₂—CH₂O)₃]₃Si(CH₂)₃SH,
[(C₁₅H₃₁O—(CH₂—CH₂O)₄]₃Si(CH₂)₃SH,
[(C₁₅H₃₁O—(CH₂—CH₂O)₅]₃Si(CH₂)₃SH,
[(C₁₅H₃₁O—(CH₂—CH₂O)₆]₃Si(CH₂)₃SH,
[(C₁₆H₃₃O—(CH₂—CH₂O)₂]₃Si(CH₂)₃SH,
[(C₁₆H₃₃O—(CH₂—CH₂O)₃]₃Si(CH₂)₃SH,
[(C₁₆H₃₃O—(CH₂—CH₂O)₄]₃Si(CH₂)₃SH,
[(C₁₆H₃₃O—(CH₂—CH₂O)₅]₃Si(CH₂)₃SH,
[(C₁₆H₃₃O—(CH₂—CH₂O)₆]₃Si(CH₂)₃SH,
[(C₁₇H₃₅O—(CH₂—CH₂O)₂]₃Si(CH₂)₃SH,
[(C₁₇H₃₅O—(CH₂—CH₂O)₃]₃Si(CH₂)₃SH,
[(C₁₇H₃₅O—(CH₂—CH₂O)₄]₃Si(CH₂)₃SH,
[(C₁₇H₃₅O—(CH₂—CH₂O)₅]₃Si(CH₂)₃SH,
[(C₁₇H₃₅O—(CH₂—CH₂O)₆]₃Si(CH₂)₃SH,
[(C₁₂H₂₅O—(CH₂—CH₂O)₂](EtO)₂Si—CH₂—CH(CH₃)—CH₂—SH,
[(C₁₂H₂₅O—(CH₂—CH₂O)₃](EtO)₂Si—CH₂—CH(CH₃)—CH₂—SH,
[(C₁₂H₂₅O—(CH₂—CH₂O)₄](EtO)₂Si—CH₂—CH(CH₃)—CH₂—SH,
[(C₁₂H₂₅O—(CH₂—CH₂O)₅](EtO)₂Si—CH₂—CH(CH₃)—CH₂—SH,
[(C₁₂H₂₅O—(CH₂—CH₂O)₆](EtO)₂Si—CH₂—CH(CH₃)—CH₂—SH,
[(C₁₃H₂₇O—(CH₂—CH₂O)₂](EtO)₂Si—CH₂—CH(CH₃)—CH₂—SH,
[(C₁₃H₂₇O—(CH₂—CH₂O)₃](EtO)₂Si—CH₂—CH(CH₃)—CH₂—SH,
[(C₁₃H₂₇O—(CH₂—CH₂O)₄](EtO)₂Si—CH₂—CH(CH₃)—CH₂—SH,
[(C₁₃H₂₇O—(CH₂—CH₂O)₅](EtO)₂Si—CH₂—CH(CH₃)—CH₂—SH,
[(C₁₃H₂₇O—(CH₂—CH₂O)₆](EtO)₂Si—CH₂—CH(CH₃)—CH₂—SH,
[(C₁₄H₂₉O—(CH₂—CH₂O)₂](EtO)₂Si—CH₂—CH(CH₃)—CH₂—SH,
[(C₁₄H₂₉O—(CH₂—CH₂O)₃](EtO)₂Si—CH₂—CH(CH₃)—CH₂—SH,
[(C₁₄H₂₉O—(CH₂—CH₂O)₄](EtO)₂Si—CH₂—CH(CH₃)—CH₂—SH,
[(C₁₄H₂₉O—(CH₂—CH₂O)₅](EtO)₂Si—CH₂—CH(CH₃)—CH₂—SH,
[(C₁₄H₂₉O—(CH₂—CH₂O)₆](EtO)₂Si—CH₂—CH(CH₃)—CH₂—SH,
[(C₁₅H₃₁O—(CH₂—CH₂O)₂](EtO)₂Si—CH₂—CH(CH₃)—CH₂—SH,
[(C₁₅H₃₁O—(CH₂—CH₂O)₃](EtO)₂Si—CH₂—CH(CH₃)—CH₂—SH,
[(C₁₅H₃₁O—(CH₂—CH₂O)₄](EtO)₂Si—CH₂—CH(CH₃)—CH₂—SH,
[(C₁₅H₃₁O—(CH₂—CH₂O)₅](EtO)₂Si—CH₂—CH(CH₃)—CH₂—SH,
[(C₁₅H₃₁O—(CH₂—CH₂O)₆](EtO)₂Si—CH₂—CH(CH₃)—CH₂—SH,
[(C₁₆H₃₃O—(CH₂—CH₂O)₂](EtO)₂Si—CH₂—CH(CH₃)—CH₂—SH,
[(C₁₆H₃₃O—(CH₂—CH₂O)₃](EtO)₂Si—CH₂—CH(CH₃)—CH₂—SH,
[(C₁₆H₃₃O—(CH₂—CH₂O)₄](EtO)₂Si—CH₂—CH(CH₃)—CH₂—SH,
[(C₁₆H₃₃O—(CH₂—CH₂O)₅](EtO)₂Si—CH₂—CH(CH₃)—CH₂—SH,
[(C₁₆H₃₃O—(CH₂—CH₂O)₆](EtO)₂Si—CH₂—CH(CH₃)—CH₂—SH,
[(C₁₂H₂₅O—(CH₂—CH₂O)₂]₂(EtO)Si—CH₂—CH(CH₃)—CH₂—SH,
[(C₁₂H₂₅O—(CH₂—CH₂O)₃]₂(EtO)Si—CH₂—CH(CH₃)—CH₂—SH,
[(C₁₂H₂₅O—(CH₂—CH₂O)₄]₂(EtO)Si—CH₂—CH(CH₃)—CH₂—SH,
[(C₁₂H₂₅O—(CH₂—CH₂O)₅]₂(EtO)Si—CH₂—CH(CH₃)—CH₂—SH,
[(C₁₂H₂₅O—(CH₂—CH₂O)₆]₂(EtO)Si—CH₂—CH(CH₃)—CH₂—SH,
[(C₁₃H₂₇O—(CH₂—CH₂O)₂]₂(EtO)Si—CH₂—CH(CH₃)—CH₂—SH,
[(C₁₃H₂₇O—(CH₂—CH₂O)₃]₂(EtO)Si—CH₂—CH(CH₃)—CH₂—SH,
[(C₁₃H₂₇O—(CH₂—CH₂O)₄]₂(EtO)Si—CH₂—CH(CH₃)—CH₂—SH,
[(C₁₃H₂₇O—(CH₂—CH₂O)₅]₂(EtO)Si—CH₂—CH(CH₃)—CH₂—SH,

[(C$_{13}$H$_{27}$O—(CH$_2$—CH$_2$O)$_6$]$_2$(EtO)Si—CH$_2$—CH(CH$_3$)—CH$_2$—SH,

[(C$_{14}$H$_{29}$O—(CH$_2$—CH$_2$O)$_2$]$_2$(EtO)Si—CH$_2$—CH(CH$_3$)—CH$_2$—SH,

[(C$_{14}$H$_{29}$O—(CH$_2$—CH$_2$O)$_3$]$_2$(EtO)Si—CH$_2$—CH(CH$_3$)—CH$_2$—SH,

[(C$_{14}$H$_{29}$O—(CH$_2$—CH$_2$O)$_4$]$_2$(EtO)Si—CH$_2$—CH(CH$_3$)—CH$_2$—SH,

[(C$_{14}$H$_{29}$O—(CH$_2$—CH$_2$O)$_5$]$_2$(EtO)Si—CH$_2$—CH(CH$_3$)—CH$_2$—SH,

[(C$_{14}$H$_{29}$O—(CH$_2$—CH$_2$O)$_6$]$_2$(EtO)Si—CH$_2$—CH(CH$_3$)—CH$_2$—SH,

[(C$_{15}$H$_{31}$O—(CH$_2$—CH$_2$O)$_2$]$_2$(EtO)Si—CH$_2$—CH(CH$_3$)—CH$_2$—SH,

[(C$_{15}$H$_{31}$O—(CH$_2$—CH$_2$O)$_3$]$_2$(EtO)Si—CH$_2$—CH(CH$_3$)—CH$_2$—SH,

[(C$_{15}$H$_{31}$O—(CH$_2$—CH$_2$O)$_4$]$_2$(EtO)Si—CH$_2$—CH(CH$_3$)—CH$_2$—SH,

[(C$_{15}$H$_{31}$O—(CH$_2$—CH$_2$O)$_5$]$_2$(EtO)Si—CH$_2$—CH(CH$_3$)—CH$_2$—SH,

[(C$_{15}$H$_{31}$O—(CH$_2$—CH$_2$O)$_6$]$_2$(EtO)Si—CH$_2$—CH(CH$_3$)—CH$_2$—SH,

[(C$_{16}$H$_{33}$O—(CH$_2$—CH$_2$O)$_2$]$_2$(EtO)Si—CH$_2$—CH(CH$_3$)—CH$_2$—SH,

[(C$_{16}$H$_{33}$O—(CH$_2$—CH$_2$O)$_3$]$_2$(EtO)Si—CH$_2$—CH(CH$_3$)—CH$_2$—SH,

[(C$_{16}$H$_{33}$O—(CH$_2$—CH$_2$O)$_4$]$_2$(EtO)Si—CH$_2$—CH(CH$_3$)—CH$_2$—SH,

[(C$_{16}$H$_{33}$O—(CH$_2$—CH$_2$O)$_5$]$_2$(EtO)Si—CH$_2$—CH(CH$_3$)—CH$_2$—SH,

[(C$_{16}$H$_{33}$O—(CH$_2$—CH$_2$O)$_6$]$_2$(EtO)Si—CH$_2$—CH(CH$_3$)—CH$_2$—SH,

[(C$_{12}$H$_{25}$O—(CH$_2$—CH$_2$O)$_2$]$_2$(HO)Si—CH$_2$—CH(CH$_3$)—CH$_2$—SH,

[(C$_{12}$H$_{25}$O—(CH$_2$—CH$_2$O)$_3$]$_2$(HO)Si—CH$_2$—CH(CH$_3$)—CH$_2$—SH,

[(C$_{12}$H$_{25}$O—(CH$_2$—CH$_2$O)$_4$]$_2$(HO)Si—CH$_2$—CH(CH$_3$)—CH$_2$—SH,

[(C$_{12}$H$_{25}$O—(CH$_2$—CH$_2$O)$_5$]$_2$(HO)Si—CH$_2$—CH(CH$_3$)—CH$_2$—SH,

[(C$_{12}$H$_{25}$O—(CH$_2$—CH$_2$O)$_6$]$_2$(HO)Si—CH$_2$—CH(CH$_3$)—CH$_2$—SH,

[(C$_{13}$H$_{27}$O—(CH$_2$—CH$_2$O)$_2$]$_2$(HO)Si—CH$_2$—CH(CH$_3$)—CH$_2$—SH,

[(C$_{13}$H$_{27}$O—(CH$_2$—CH$_2$O)$_3$]$_2$(HO)Si—CH$_2$—CH(CH$_3$)—CH$_2$—SH,

[(C$_{13}$H$_{27}$O—(CH$_2$—CH$_2$O)$_4$]$_2$(HO)Si—CH$_2$—CH(CH$_3$)—CH$_2$—SH,

[(C$_{13}$H$_{27}$O—(CH$_2$—CH$_2$O)$_5$]$_2$(HO)Si—CH$_2$—CH(CH$_3$)—CH$_2$—SH,

[(C$_{13}$H$_{27}$O—(CH$_2$—CH$_2$O)$_6$]$_2$(HO)Si—CH$_2$—CH(CH$_3$)—CH$_2$—SH,

[(C$_{14}$H$_{29}$O—(CH$_2$—CH$_2$O)$_2$]$_2$(HO)Si—CH$_2$—CH(CH$_3$)—CH$_2$—SH,

[(C$_{14}$H$_{29}$O—(CH$_2$—CH$_2$O)$_3$]$_2$(HO)Si—CH$_2$—CH(CH$_3$)—CH$_2$—SH,

[(C$_{14}$H$_{29}$O—(CH$_2$—CH$_2$O)$_4$]$_2$(HO)Si—CH$_2$—CH(CH$_3$)—CH$_2$—SH,

[(C$_{14}$H$_{29}$O—(CH$_2$—CH$_2$O)$_5$]$_2$(HO)Si—CH$_2$—CH(CH$_3$)—CH$_2$—SH,

[(C$_{14}$H$_{29}$O—(CH$_2$—CH$_2$O)$_6$]$_2$(HO)Si—CH$_2$—CH(CH$_3$)—CH$_2$—SH,

[(C$_{15}$H$_{31}$O—(CH$_2$—CH$_2$O)$_2$]$_2$(HO)Si—CH$_2$—CH(CH$_3$)—CH$_2$—SH,

[(C$_{15}$H$_{31}$O—(CH$_2$—CH$_2$O)$_3$]$_2$(HO)Si—CH$_2$—CH(CH$_3$)—CH$_2$—SH,

[(C$_{15}$H$_{31}$O—(CH$_2$—CH$_2$O)$_4$]$_2$(HO)Si—CH$_2$—CH(CH$_3$)—CH$_2$—SH,

[(C$_{15}$H$_{31}$O—(CH$_2$—CH$_2$O)$_5$]$_2$(HO)Si—CH$_2$—CH(CH$_3$)—CH$_2$—SH,

[(C$_{15}$H$_{31}$O—(CH$_2$—CH$_2$O)$_6$]$_2$(HO)Si—CH$_2$—CH(CH$_3$)—CH$_2$—SH,

[(C$_{16}$H$_{33}$O—(CH$_2$—CH$_2$O)$_2$]$_2$(HO)Si—CH$_2$—CH(CH$_3$)—CH$_2$—SH,

[(C$_{16}$H$_{33}$O—(CH$_2$—CH$_2$O)$_3$]$_2$(HO)Si—CH$_2$—CH(CH$_3$)—CH$_2$—SH,

[(C$_{16}$H$_{33}$O—(CH$_2$—CH$_2$O)$_4$]$_2$(HO)Si—CH$_2$—CH(CH$_3$)—CH$_2$—SH,

[(C$_{16}$H$_{33}$O—(CH$_2$—CH$_2$O)$_5$]$_2$(HO)Si—CH$_2$—CH(CH$_3$)—CH$_2$—SH,

[(C$_{16}$H$_{33}$O—(CH$_2$—CH$_2$O)$_6$]$_2$(HO)Si—CH$_2$—CH(CH$_3$)—CH$_2$—SH,

[(C$_{12}$H$_{25}$O—(CH$_2$—CH$_2$O)$_2$]$_3$Si—CH$_2$—CH(CH$_3$)—CH$_2$—SH,

[(C$_{12}$H$_{25}$O—(CH$_2$—CH$_2$O)$_3$]$_3$Si—CH$_2$—CH(CH$_3$)—CH$_2$—SH,

[(C$_{12}$H$_{25}$O—(CH$_2$—CH$_2$O)$_4$]$_3$Si—CH$_2$—CH(CH$_3$)—CH$_2$—SH,

[(C$_{12}$H$_{25}$O—(CH$_2$—CH$_2$O)$_5$]$_3$Si—CH$_2$—CH(CH$_3$)—CH$_2$—SH,

[(C$_{12}$H$_{25}$O—(CH$_2$—CH$_2$O)$_6$]$_3$Si—CH$_2$—CH(CH$_3$)—CH$_2$—SH,

[(C$_{13}$H$_{27}$O—(CH$_2$—CH$_2$O)$_2$]$_3$Si—CH$_2$—CH(CH$_3$)—CH$_2$—SH,

[(C$_{13}$H$_{27}$O—(CH$_2$—CH$_2$O)$_3$]$_3$Si—CH$_2$—CH(CH$_3$)—CH$_2$—SH,

[(C$_{13}$H$_{27}$O—(CH$_2$—CH$_2$O)$_4$]$_3$Si—CH$_2$—CH(CH$_3$)—CH$_2$—SH,

[(C$_{13}$H$_{27}$O—(CH$_2$—CH$_2$O)$_5$]$_3$Si—CH$_2$—CH(CH$_3$)—CH$_2$—SH,

[(C$_{13}$H$_{27}$O—(CH$_2$—CH$_2$O)$_6$]$_3$Si—CH$_2$—CH(CH$_3$)—CH$_2$—SH,

[(C$_{14}$H$_{29}$O—(CH$_2$—CH$_2$O)$_2$]$_3$Si—CH$_2$—CH(CH$_3$)—CH$_2$—SH,

[(C$_{14}$H$_{29}$O—(CH$_2$—CH$_2$O)$_3$]$_3$Si—CH$_2$—CH(CH$_3$)—CH$_2$—SH,

[(C$_{14}$H$_{29}$O—(CH$_2$—CH$_2$O)$_4$]$_3$Si—CH$_2$—CH(CH$_3$)—CH$_2$—SH,

[(C$_{14}$H$_{29}$O—(CH$_2$—CH$_2$O)$_5$]$_3$Si—CH$_2$—CH(CH$_3$)—CH$_2$—SH,

[(C$_{14}$H$_{29}$O—(CH$_2$—CH$_2$O)$_6$]$_3$Si—CH$_2$—CH(CH$_3$)—CH$_2$—SH,

[(C$_{15}$H$_{31}$O—(CH$_2$—CH$_2$O)$_2$]$_3$Si—CH$_2$—CH(CH$_3$)—CH$_2$—SH,

[(C$_{15}$H$_{31}$O—(CH$_2$—CH$_2$O)$_3$]$_3$Si—CH$_2$—CH(CH$_3$)—CH$_2$—SH,

[(C$_{15}$H$_{31}$O—(CH$_2$—CH$_2$O)$_4$]$_3$Si—CH$_2$—CH(CH$_3$)—CH$_2$—SH,

[(C$_{15}$H$_{31}$O—(CH$_2$—CH$_2$O)$_5$]$_3$Si—CH$_2$—CH(CH$_3$)—CH$_2$—SH,

[(C$_{15}$H$_{31}$O—(CH$_2$—CH$_2$O)$_6$]$_3$Si—CH$_2$—CH(CH$_3$)—CH$_2$—SH,

[(C$_{16}$H$_{33}$O—(CH$_2$—CH$_2$O)$_2$]$_3$Si—CH$_2$—CH(CH$_3$)—CH$_2$—SH,

[(C$_{16}$H$_{33}$O—(CH$_2$—CH$_2$O)$_3$]$_3$Si—CH$_2$—CH(CH$_3$)—CH$_2$—SH,

[(C$_{16}$H$_{33}$O—(CH$_2$—CH$_2$O)$_4$]$_3$Si—CH$_2$—CH(CH$_3$)—CH$_2$—SH,

[(C$_{16}$H$_{33}$O—(CH$_2$—CH$_2$O)$_5$]$_3$Si—CH$_2$—CH(CH$_3$)—CH$_2$—SH, or

[(C$_{16}$H$_{33}$O—(CH$_2$—CH$_2$O)$_6$]$_3$Si—CH$_2$—CH(CH$_3$)—CH$_2$—SH, wherein the alkyl chains $C_{11}$-$C_{17}$ can be linear or branched.

Examples of preferred compounds of the formula I with $R^2$=CN include the following:

[($C_{11}H_{23}$O—($CH_2$—$CH_2$O)$_2$]Me$_2$Si($CH_2$)$_3$SCN,
[($C_{11}H_{23}$O—($CH_2$—$CH_2$O)$_3$]Me$_2$Si($CH_2$)$_3$SCN,
[($C_{11}H_{23}$O—($CH_2$—$CH_2$O)$_4$]Me$_2$Si($CH_2$)$_3$SCN,
[($C_{11}H_{23}$O—($CH_2$—$CH_2$O)$_5$]Me$_2$Si($CH_2$)$_3$SCN,
[($C_{11}H_{23}$O—($CH_2$—$CH_2$O)$_6$]Me$_2$Si($CH_2$)$_3$SCN,
[($C_{12}H_{25}$O—($CH_2$—$CH_2$O)$_2$]Me$_2$Si($CH_2$)$_3$SCN,
[($C_{12}H_{25}$O—($CH_2$—$CH_2$O)$_3$]Me$_2$Si($CH_2$)$_3$SCN,
[($C_{12}H_{25}$O—($CH_2$—$CH_2$O)$_4$]Me$_2$Si($CH_2$)$_3$SCN,
[($C_{12}H_{25}$O—($CH_2$—$CH_2$O)$_5$]Me$_2$Si($CH_2$)$_3$SCN,
[($C_{12}H_{25}$O—($CH_2$—$CH_2$O)$_6$]Me$_2$Si($CH_2$)$_3$SCN,
[($C_{13}H_{27}$O—($CH_2$—$CH_2$O)$_2$]Me$_2$Si($CH_2$)$_3$SCN,
[($C_{13}H_{27}$O—($CH_2$—$CH_2$O)$_3$]Me$_2$Si($CH_2$)$_3$SCN,
[($C_{13}H_{27}$O—($CH_2$—$CH_2$O)$_4$]Me$_2$Si($CH_2$)$_3$SCN,
[($C_{13}H_{27}$O—($CH_2$—$CH_2$O)$_5$]Me$_2$Si($CH_2$)$_3$SCN,
[($C_{13}H_{27}$O—($CH_2$—$CH_2$O)$_6$]Me$_2$Si($CH_2$)$_3$SCN,
[($C_{14}H_{29}$O—($CH_2$—$CH_2$O)$_2$]Me$_2$Si($CH_2$)$_3$SCN,
[($C_{14}H_{29}$O—($CH_2$—$CH_2$O)$_3$]Me$_2$Si($CH_2$)$_3$SCN,
[($C_{14}H_{29}$O—($CH_2$—$CH_2$O)$_4$]Me$_2$Si($CH_2$)$_3$SCN,
[($C_{14}H_{29}$O—($CH_2$—$CH_2$O)$_5$]Me$_2$Si($CH_2$)$_3$SCN,
[($C_{14}H_{29}$O—($CH_2$—$CH_2$O)$_6$]Me$_2$Si($CH_2$)$_3$SCN,
[($C_{11}H_{23}$O—($CH_2$—$CH_2$O)$_2$](MeO)$_2$Si($CH_2$)$_3$SCN,
[($C_{11}H_{23}$O—($CH_2$—$CH_2$O)$_3$](MeO)$_2$Si($CH_2$)$_3$SCN,
[($C_{11}H_{23}$O—($CH_2$—$CH_2$O)$_4$](MeO)$_2$Si($CH_2$)$_3$SCN,
[($C_{11}H_{23}$O—($CH_2$—$CH_2$O)$_5$](MeO)$_2$Si($CH_2$)$_3$SCN,
[($C_{11}H_{23}$O—($CH_2$—$CH_2$O)$_6$](MeO)$_2$Si($CH_2$)$_3$SCN,
[($C_{12}H_{25}$O—($CH_2$—$CH_2$O)$_2$](MeO)$_2$Si($CH_2$)$_3$SCN,
[($C_{12}H_{25}$O—($CH_2$—$CH_2$O)$_3$](MeO)$_2$Si($CH_2$)$_3$SCN,
[($C_{12}H_{25}$O—($CH_2$—$CH_2$O)$_4$](MeO)$_2$Si($CH_2$)$_3$SCN,
[($C_{12}H_{25}$O—($CH_2$—$CH_2$O)$_5$](MeO)$_2$Si($CH_2$)$_3$SCN,
[($C_{12}H_{25}$O—($CH_2$—$CH_2$O)$_6$](MeO)$_2$Si($CH_2$)$_3$SCN,
[($C_{13}H_{27}$O—($CH_2$—$CH_2$O)$_2$](MeO)$_2$Si($CH_2$)$_3$SCN,
[($C_{13}H_{27}$O—($CH_2$—$CH_2$O)$_3$](MeO)$_2$Si($CH_2$)$_3$SCN,
[($C_{13}H_{27}$O—($CH_2$—$CH_2$O)$_4$](MeO)$_2$Si($CH_2$)$_3$SCN,
[($C_{13}H_{27}$O—($CH_2$—$CH_2$O)$_5$](MeO)$_2$Si($CH_2$)$_3$SCN,
[($C_{13}H_{27}$O—($CH_2$—$CH_2$O)$_6$](MeO)$_2$Si($CH_2$)$_3$SCN,
[($C_{14}H_{29}$O—($CH_2$—$CH_2$O)$_2$](MeO)$_2$Si($CH_2$)$_3$SCN,
[($C_{14}H_{29}$O—($CH_2$—$CH_2$O)$_3$](MeO)$_2$Si($CH_2$)$_3$SCN,
[($C_{14}H_{29}$O—($CH_2$—$CH_2$O)$_4$](MeO)$_2$Si($CH_2$)$_3$SCN,
[($C_{14}H_{29}$O—($CH_2$—$CH_2$O)$_5$](MeO)$_2$Si($CH_2$)$_3$SCN,
[($C_{14}H_{29}$O—($CH_2$—$CH_2$O)$_6$](MeO)$_2$Si($CH_2$)$_3$SCN,
[($C_{11}H_{23}$O—($CH_2$—$CH_2$O)$_2$]$_2$(MeO)Si($CH_2$)$_3$SCN,
[($C_{11}H_{23}$O—($CH_2$—$CH_2$O)$_3$]$_2$(MeO)Si($CH_2$)$_3$SCN,
[($C_{11}H_{23}$O—($CH_2$—$CH_2$O)$_4$]$_2$(MeO)Si($CH_2$)$_3$SCN,
[($C_{11}H_{23}$O—($CH_2$—$CH_2$O)$_5$]$_2$(MeO)Si($CH_2$)$_3$SCN,
[($C_{11}H_{23}$O—($CH_2$—$CH_2$O)$_6$]$_2$(MeO)Si($CH_2$)$_3$SCN,
[($C_{12}H_{25}$O—($CH_2$—$CH_2$O)$_2$]$_2$(MeO)Si($CH_2$)$_3$SCN,
[($C_{12}H_{25}$O—($CH_2$—$CH_2$O)$_3$]$_2$(MeO)Si($CH_2$)$_3$SCN,
[($C_{12}H_{25}$O—($CH_2$—$CH_2$O)$_4$]$_2$(MeO)Si($CH_2$)$_3$SCN,
[($C_{12}H_{25}$O—($CH_2$—$CH_2$O)$_5$]$_2$(MeO)Si($CH_2$)$_3$SCN,
[($C_{12}H_{25}$O—($CH_2$—$CH_2$O)$_6$]$_2$(MeO)Si($CH_2$)$_3$SCN,
[($C_{13}H_{27}$O—($CH_2$—$CH_2$O)$_2$]$_2$(MeO)Si($CH_2$)$_3$SCN,
[($C_{13}H_{27}$O—($CH_2$—$CH_2$O)$_3$]$_2$(MeO)Si($CH_2$)$_3$SCN,
[($C_{13}H_{27}$O—($CH_2$—$CH_2$O)$_4$]$_2$(MeO)Si($CH_2$)$_3$SCN,
[($C_{13}H_{27}$O—($CH_2$—$CH_2$O)$_5$]$_2$(MeO)Si($CH_2$)$_3$SCN,
[($C_{13}H_{27}$O—($CH_2$—$CH_2$O)$_6$]$_2$(MeO)Si($CH_2$)$_3$SCN,
[($C_{14}H_{29}$O—($CH_2$—$CH_2$O)$_2$]$_2$(MeO)Si($CH_2$)$_3$SCN,
[($C_{14}H_{29}$O—($CH_2$—$CH_2$O)$_3$]$_2$(MeO)Si($CH_2$)$_3$SCN,
[($C_{14}H_{29}$O—($CH_2$—$CH_2$O)$_4$]$_2$(MeO)Si($CH_2$)$_3$SCN,
[($C_{14}H_{29}$O—($CH_2$—$CH_2$O)$_5$]$_2$(MeO)Si($CH_2$)$_3$SCN,
[($C_{14}H_{29}$O—($CH_2$—$CH_2$O)$_6$]$_2$(MeO)Si($CH_2$)$_3$SCN,
[($C_{11}H_{23}$O—($CH_2$—$CH_2$O)$_2$](EtO)$_2$Si($CH_2$)$_3$SCN,
[($C_{11}H_{23}$O—($CH_2$—$CH_2$O)$_3$](EtO)$_2$Si($CH_2$)$_3$SCN,
[($C_{11}H_{23}$O—($CH_2$—$CH_2$O)$_4$](EtO)$_2$Si($CH_2$)$_3$SCN,
[($C_{11}H_{23}$O—($CH_2$—$CH_2$O)$_5$](EtO)$_2$Si($CH_2$)$_3$SCN,
[($C_{11}H_{23}$O—($CH_2$—$CH_2$O)$_6$](EtO)$_2$Si($CH_2$)$_3$SCN,
[($C_{12}H_{25}$O—($CH_2$—$CH_2$O)$_2$](EtO)$_2$Si($CH_2$)$_3$SCN,
[($C_{12}H_{25}$O—($CH_2$—$CH_2$O)$_3$](EtO)$_2$Si($CH_2$)$_3$SCN,
[($C_{12}H_{25}$O—($CH_2$—$CH_2$O)$_4$](EtO)$_2$Si($CH_2$)$_3$SCN,
[($C_{12}H_{25}$O—($CH_2$—$CH_2$O)$_5$](EtO)$_2$Si($CH_2$)$_3$SCN,
[($C_{12}H_{25}$O—($CH_2$—$CH_2$O)$_6$](EtO)$_2$Si($CH_2$)$_3$SCN,
[($C_{13}H_{27}$O—($CH_2$—$CH_2$O)$_2$](EtO)$_2$Si($CH_2$)$_3$SCN,
[($C_{13}H_{27}$O—($CH_2$—$CH_2$O)$_3$](EtO)$_2$Si($CH_2$)$_3$SCN,
[($C_{13}H_{27}$O—($CH_2$—$CH_2$O)$_4$](EtO)$_2$Si($CH_2$)$_3$SCN,
[($C_{13}H_{27}$O—($CH_2$—$CH_2$O)$_5$](EtO)$_2$Si($CH_2$)$_3$SCN,
[($C_{13}H_{27}$O—($CH_2$—$CH_2$O)$_6$](EtO)$_2$Si($CH_2$)$_3$SCN,
[($C_{14}H_{29}$O—($CH_2$—$CH_2$O)$_2$](EtO)$_2$Si($CH_2$)$_3$SCN,
[($C_{14}H_{29}$O—($CH_2$—$CH_2$O)$_3$](EtO)$_2$Si($CH_2$)$_3$SCN,
[($C_{14}H_{29}$O—($CH_2$—$CH_2$O)$_4$](EtO)$_2$Si($CH_2$)$_3$SCN,
[($C_{14}H_{29}$O—($CH_2$—$CH_2$O)$_5$](EtO)$_2$Si($CH_2$)$_3$SCN,
[($C_{14}H_{29}$O—($CH_2$—$CH_2$O)$_6$](EtO)$_2$Si($CH_2$)$_3$SCN,
[($C_{11}H_{23}$O—($CH_2$—$CH_2$O)$_2$]$_2$(EtO)Si($CH_2$)$_3$SCN,
[($C_{11}H_{23}$O—($CH_2$—$CH_2$O)$_3$]$_2$(EtO)Si($CH_2$)$_3$SCN,
[($C_{11}H_{23}$O—($CH_2$—$CH_2$O)$_4$]$_2$(EtO)Si($CH_2$)$_3$SCN,
[($C_{11}H_{23}$O—($CH_2$—$CH_2$O)$_5$]$_2$(EtO)Si($CH_2$)$_3$SCN,
[($C_{11}H_{23}$O—($CH_2$—$CH_2$O)$_6$]$_2$(EtO)Si($CH_2$)$_3$SCN,
[($C_{12}H_{25}$O—($CH_2$—$CH_2$O)$_2$]$_2$(EtO)Si($CH_2$)$_3$SCN,
[($C_{12}H_{25}$O—($CH_2$—$CH_2$O)$_3$]$_2$(EtO)Si($CH_2$)$_3$SCN,
[($C_{12}H_{25}$O—($CH_2$—$CH_2$O)$_4$]$_2$(EtO)Si($CH_2$)$_3$SCN,
[($C_{12}H_{25}$O—($CH_2$—$CH_2$O)$_5$]$_2$(EtO)Si($CH_2$)$_3$SCN,
[($C_{12}H_{25}$O—($CH_2$—$CH_2$O)$_6$]$_2$(EtO)Si($CH_2$)$_3$SCN,
[($C_{13}H_{27}$O—($CH_2$—$CH_2$O)$_2$]$_2$(EtO)Si($CH_2$)$_3$SCN,
[($C_{13}H_{27}$O—($CH_2$—$CH_2$O)$_3$]$_2$(EtO)Si($CH_2$)$_3$SCN,
[($C_{13}H_{27}$O—($CH_2$—$CH_2$O)$_4$]$_2$(EtO)Si($CH_2$)$_3$SCN,
[($C_{13}H_{27}$O—($CH_2$—$CH_2$O)$_5$]$_2$(EtO)Si($CH_2$)$_3$SCN,
[($C_{13}H_{27}$O—($CH_2$—$CH_2$O)$_6$]$_2$(EtO)Si($CH_2$)$_3$SCN,
[($C_{14}H_{29}$O—($CH_2$—$CH_2$O)$_2$]$_2$(EtO)Si($CH_2$)$_3$SCN,
[($C_{14}H_{29}$O—($CH_2$—$CH_2$O)$_3$]$_2$(EtO)Si($CH_2$)$_3$SCN,
[($C_{14}H_{29}$O—($CH_2$—$CH_2$O)$_4$]$_2$(EtO)Si($CH_2$)$_3$ SCN,
[($C_{14}H_{29}$O—($CH_2$—$CH_2$O)$_5$]$_2$(EtO)Si($CH_2$)$_3$SCN,
[($C_{14}H_{29}$O—($CH_2$—$CH_2$O)$_6$]$_2$(EtO)Si($CH_2$)$_3$SCN,
[($C_{11}H_{23}$O—($CH_2$—$CH_2$O)$_2$]$_3$Si($CH_2$)$_3$SCN,
[($C_{11}H_{23}$O—($CH_2$—$CH_2$O)$_3$]$_3$Si($CH_2$)$_3$SCN,
[($C_{11}H_{23}$O—($CH_2$—$CH_2$O)$_4$]$_3$Si($CH_2$)$_3$SCN,
[($C_{11}H_{23}$O—($CH_2$—$CH_2$O)$_5$]$_3$Si($CH_2$)$_3$SCN,
[($C_{11}H_{23}$O—($CH_2$—$CH_2$O)$_6$]$_3$Si($CH_2$)$_3$SCN,
[($C_{12}H_{25}$O—($CH_2$—$CH_2$O)$_2$]$_3$Si($CH_2$)$_3$SCN,
[($C_{12}H_{25}$O—($CH_2$—$CH_2$O)$_3$]$_3$Si($CH_2$)$_3$SCN,
[($C_{12}H_{25}$O—($CH_2$—$CH_2$O)$_4$]$_3$Si($CH_2$)$_3$SCN,
[($C_{12}H_{25}$O—($CH_2$—$CH_2$O)$_5$]$_3$Si($CH_2$)$_3$SCN,
[($C_{12}H_{25}$O—($CH_2$—$CH_2$O)$_6$]$_3$Si($CH_2$)$_3$SCN,
[($C_{13}H_{27}$O—($CH_2$—$CH_2$O)$_2$]$_3$Si($CH_2$)$_3$SCN,
[($C_{13}H_{27}$O—($CH_2$—$CH_2$O)$_3$]$_3$Si($CH_2$)$_3$SCN,
[($C_{13}H_{27}$O—($CH_2$—$CH_2$O)$_4$]$_3$Si($CH_2$)$_3$SCN,
[($C_{13}H_{27}$O—($CH_2$—$CH_2$O)$_5$]$_3$Si($CH_2$)$_3$SCN,
[($C_{13}H_{27}$O—($CH_2$—$CH_2$O)$_6$]$_3$Si($CH_2$)$_3$SCN,
[($C_{14}H_{29}$O—($CH_2$—$CH_2$O)$_2$]$_3$Si($CH_2$)$_3$SCN,
[($C_{14}H_{29}$O—($CH_2$—$CH_2$O)$_3$]$_3$Si($CH_2$)$_3$SCN,
[($C_{14}H_{29}$O—($CH_2$—$CH_2$O)$_4$]$_3$Si($CH_2$)$_3$SCN,
[($C_{14}H_{29}$O—($CH_2$—$CH_2$O)$_5$]$_3$Si($CH_2$)$_3$SCN or
[($C_{14}H_{29}$O—($CH_2$—$CH_2$O)$_6$]$_3$Si($CH_2$)$_3$SCN, wherein the alkyl chains $C_{11}$-$C_{14}$ can be linear or branched.

Examples of preferred compounds of the formula I with $R^2$=—C(=O)—$R^4$ and $R^4$=—$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$ and —$C_6H_5$ (phenyl) include the following:

[($C_{11}H_{23}$O—($CH_2$—$CH_2$O)$_2$]Me$_2$Si($CH_2$)$_3$—S—C(=O)—$R^4$,

[($C_{11}H_{23}$O—($CH_2$—$CH_2$O)$_3$]Me$_2$Si($CH_2$)$_3$—S—C(=O)—$R^4$,

[(C$_{11}$H$_{23}$O—(CH$_2$—CH$_2$O)$_4$]Me$_2$Si(CH$_2$)$_3$—S—C(=O)—R$^4$,
[(C$_{11}$H$_{23}$O—(CH$_2$—CH$_2$O)$_5$]Me$_2$Si(CH$_2$)$_3$—S—C(=O)—R$^4$,
[(C$_{11}$H$_{23}$O—(CH$_2$—CH$_2$O)$_6$]Me$_2$Si(CH$_2$)$_3$—S—C(=O)—R$^4$,
[(C$_{12}$H$_{25}$O—(CH$_2$—CH$_2$O)$_2$]Me$_2$Si(CH$_2$)$_3$—S—C(=O)—R$^4$,
[(C$_{12}$H$_{25}$O—(CH$_2$—CH$_2$O)$_3$]Me$_2$Si(CH$_2$)$_3$—S—C(=O)—R$^4$,
[(C$_{12}$H$_{25}$O—(CH$_2$—CH$_2$O)$_4$]Me$_2$Si(CH$_2$)$_3$—S—C(=O)—R$^4$,
[(C$_{12}$H$_{25}$O—(CH$_2$—CH$_2$O)$_5$]Me$_2$Si(CH$_2$)$_3$—S—C(=O)—R$^4$,
[(C$_{12}$H$_{25}$O—(CH$_2$—CH$_2$O)$_6$]Me$_2$Si(CH$_2$)$_3$—S—C(=O)—R$^4$,
[(C$_{13}$H$_{27}$O—(CH$_2$—CH$_2$O)$_2$]Me$_2$Si(CH$_2$)$_3$—S—C(=O)—R$^4$,
[(C$_{13}$H$_{27}$O—(CH$_2$—CH$_2$O)$_3$]Me$_2$Si(CH$_2$)$_3$—S—C(=O)—R$^4$,
[(C$_{13}$H$_{27}$O—(CH$_2$—CH$_2$O)$_4$]Me$_2$Si(CH$_2$)$_3$—S—C(=O)—R$^4$,
[(C$_{13}$H$_{27}$O—(CH$_2$—CH$_2$O)$_5$]Me$_2$Si(CH$_2$)$_3$—S—C(=O)—R$^4$,
[(C$_{13}$H$_{27}$O—(CH$_2$—CH$_2$O)$_6$]Me$_2$Si(CH$_2$)$_3$—S—C(=O)—R$^4$,
[(C$_{14}$H$_{29}$O—(CH$_2$—CH$_2$O)$_2$]Me$_2$Si(CH$_2$)$_3$—S—C(=O)—R$^4$,
[(C$_{14}$H$_{29}$O—(CH$_2$—CH$_2$O)$_3$]Me$_2$Si(CH$_2$)$_3$—S—C(=O)—R$^4$,
[(C$_{14}$H$_{29}$O—(CH$_2$—CH$_2$O)$_4$]Me$_2$Si(CH$_2$)$_3$—S—C(=O)—R$^4$,
[(C$_{14}$H$_{29}$O—(CH$_2$—CH$_2$O)$_5$]Me$_2$Si(CH$_2$)$_3$—S—C(=O)—R$^4$,
[(C$_{14}$H$_{29}$O—(CH$_2$—CH$_2$O)$_6$]Me$_2$Si(CH$_2$)$_3$—S—C(=O)—R$^4$,
[(C$_{11}$H$_{23}$O—(CH$_2$—CH$_2$O)$_2$](MeO)$_2$Si(CH$_2$)$_3$—S—C(=O)—R$^4$,
[(C$_{11}$H$_{23}$O—(CH$_2$—CH$_2$O)$_3$](MeO)$_2$Si(CH$_2$)$_3$—S—C(=O)—R$^4$,
[(C$_{11}$H$_{23}$O—(CH$_2$—CH$_2$O)$_4$](MeO)$_2$Si(CH$_2$)$_3$—S—C(=O)—R$^4$,
[(C$_{11}$H$_{23}$O—(CH$_2$—CH$_2$O)$_5$](MeO)$_2$Si(CH$_2$)$_3$—S—C(=O)—R$^4$,
[(C$_{11}$H$_{23}$O—(CH$_2$—CH$_2$O)$_6$](MeO)$_2$Si(CH$_2$)$_3$—S—C(=O)—R$^4$,
[(C$_{12}$H$_{25}$O—(CH$_2$—CH$_2$O)$_2$](MeO)$_2$Si(CH$_2$)$_3$—S—C(=O)—R$^4$,
[(C$_{12}$H$_{25}$O—(CH$_2$—CH$_2$O)$_3$](MeO)$_2$Si(CH$_2$)$_3$—S—C(=O)—R$^4$,
[(C$_{12}$H$_{25}$O—(CH$_2$—CH$_2$O)$_4$](MeO)$_2$Si(CH$_2$)$_3$—S—C(=O)—R$^4$,
[(C$_{12}$H$_{25}$O—(CH$_2$—CH$_2$O)$_5$](MeO)$_2$Si(CH$_2$)$_3$—S—C(=O)—R$^4$,
[(C$_{12}$H$_{25}$O—(CH$_2$—CH$_2$O)$_6$](MeO)$_2$Si(CH$_2$)$_3$—S—C(=O)—R$^4$,
[(C$_{13}$H$_{27}$O—(CH$_2$—CH$_2$O)$_2$](MeO)$_2$Si(CH$_2$)$_3$—S—C(=O)—R$^4$,
[(C$_{13}$H$_{27}$O—(CH$_2$—CH$_2$O)$_3$](MeO)$_2$Si(CH$_2$)$_3$—S—C(=O)—R$^4$,
[(C$_{13}$H$_{27}$O—(CH$_2$—CH$_2$O)$_4$](MeO)$_2$Si(CH$_2$)$_3$—S—C(=O)—R$^4$,
[(C$_{13}$H$_{27}$O—(CH$_2$—CH$_2$O)$_5$](MeO)$_2$Si(CH$_2$)$_3$—S—C(=O)—R$^4$,
[(C$_{13}$H$_{27}$O—(CH$_2$—CH$_2$O)$_6$](MeO)$_2$Si(CH$_2$)$_3$—S—C(=O)—R$^4$,
[(C$_{14}$H$_{29}$O—(CH$_2$—CH$_2$O)$_2$](MeO)$_2$Si(CH$_2$)$_3$—S—C(=O)—R$^4$,
[(C$_{14}$H$_{29}$O—(CH$_2$—CH$_2$O)$_3$](MeO)$_2$Si(CH$_2$)$_3$—S—C(=O)—R$^4$,
[(C$_{14}$H$_{29}$O—(CH$_2$—CH$_2$O)$_4$](MeO)$_2$Si(CH$_2$)$_3$—S—C(=O)—R$^4$,
[(C$_{14}$H$_{29}$O—(CH$_2$—CH$_2$O)$_5$](MeO)$_2$Si(CH$_2$)$_3$—S—C(=O)—R$^4$,
[(C$_{14}$H$_{29}$O—(CH$_2$—CH$_2$O)$_6$](MeO)$_2$Si(CH$_2$)$_3$—S—C(=O)—R$^4$,
[(C$_{11}$H$_{23}$O—(CH$_2$—CH$_2$O)$_2$]$_2$(MeO)Si(CH$_2$)$_3$—S—C(=O)—R$^4$,
[(C$_{11}$H$_{23}$O—(CH$_2$—CH$_2$O)$_3$]$_2$(MeO)Si(CH$_2$)$_3$—S—C(=O)—R$^4$,
[(C$_{11}$H$_{23}$O—(CH$_2$—CH$_2$O)$_4$]$_2$(MeO)Si(CH$_2$)$_3$—S—C(=O)—R$^4$,
[(C$_{11}$H$_{23}$O—(CH$_2$—CH$_2$O)$_5$]$_2$(MeO)Si(CH$_2$)$_3$—S—C(=O)—R$^4$,
[(C$_{11}$H$_{23}$O—(CH$_2$—CH$_2$O)$_6$]$_2$(MeO)Si(CH$_2$)$_3$—S—C(=O)—R$^4$,
[(C$_{12}$H$_{25}$O—(CH$_2$—CH$_2$O)$_2$]$_2$(MeO)Si(CH$_2$)$_3$—S—C(=O)—R$^4$,
[(C$_{12}$H$_{25}$O—(CH$_2$—CH$_2$O)$_3$]$_2$(MeO)Si(CH$_2$)$_3$—S—C(=O)—R$^4$,
[(C$_{12}$H$_{25}$O—(CH$_2$—CH$_2$O)$_4$]$_2$(MeO)Si(CH$_2$)$_3$—S—C(=O)—R$^4$,
[(C$_{12}$H$_{25}$O—(CH$_2$—CH$_2$O)$_5$]$_2$(MeO)Si(CH$_2$)$_3$—S—C(=O)—R$^4$,
[(C$_{12}$H$_{25}$O—(CH$_2$—CH$_2$O)$_6$]$_2$(MeO)Si(CH$_2$)$_3$—S—C(=O)—R$^4$,
[(C$_{13}$H$_{27}$O—(CH$_2$—CH$_2$O)$_2$]$_2$(MeO)Si(CH$_2$)$_3$—S—C(=O)—R$^4$,
[(C$_{13}$H$_{27}$O—(CH$_2$—CH$_2$O)$_3$]$_2$(MeO)Si(CH$_2$)$_3$—S—C(=O)—R$^4$,
[(C$_{13}$H$_{27}$O—(CH$_2$—CH$_2$O)$_4$]$_2$(MeO)Si(CH$_2$)$_3$—S—C(=O)—R$^4$,
[(C$_{13}$H$_{27}$O—(CH$_2$—CH$_2$O)$_5$]$_2$(MeO)Si(CH$_2$)$_3$—S—C(=O)—R$^4$,
[(C$_{13}$H$_{27}$O—(CH$_2$—CH$_2$O)$_6$]$_2$(MeO)Si(CH$_2$)$_3$—S—C(=O)—R$^4$,
[(C$_{14}$H$_{29}$O—(CH$_2$—CH$_2$O)$_2$]$_2$(MeO)Si(CH$_2$)$_3$—S—C(=O)—R$^4$,
[(C$_{14}$H$_{29}$O—(CH$_2$—CH$_2$O)$_3$]$_2$(MeO)Si(CH$_2$)$_3$—S—C(=O)—R$^4$,
[(C$_{14}$H$_{29}$O—(CH$_2$—CH$_2$O)$_4$]$_2$(MeO)Si(CH$_2$)$_3$—S—C(=O)—R$^4$,
[(C$_{14}$H$_{29}$O—(CH$_2$—CH$_2$O)$_5$]$_2$(MeO)Si(CH$_2$)$_3$—S—C(=O)—R$^4$,
[(C$_{14}$H$_{29}$O—(CH$_2$—CH$_2$O)$_6$]$_2$(MeO)Si(CH$_2$)$_3$—S—C(=O)—R$^4$,
[(C$_{11}$H$_{23}$O—(CH$_2$—CH$_2$O)$_2$](EtO)$_2$Si(CH$_2$)$_3$—S—C(=O)—R$^4$,
[(C$_{11}$H$_{23}$O—(CH$_2$—CH$_2$O)$_3$](EtO)$_2$Si(CH$_2$)$_3$—S—C(=O)—R$^4$,
[(C$_{11}$H$_{23}$O—(CH$_2$—CH$_2$O)$_4$](EtO)$_2$Si(CH$_2$)$_3$—S—C(=O)—R$^4$,
[(C$_{11}$H$_{23}$O—(CH$_2$—CH$_2$O)$_5$](EtO)$_2$Si(CH$_2$)$_3$—S—C(=O)—R$^4$,
[(C$_{11}$H$_{23}$O—(CH$_2$—CH$_2$O)$_6$](EtO)$_2$Si(CH$_2$)$_3$—S—C(=O)—R$^4$,
[(C$_{12}$H$_{25}$O—(CH$_2$—CH$_2$O)$_2$](EtO)$_2$Si(CH$_2$)$_3$—S—C(=O)—R$^4$,
[(C$_{12}$H$_{25}$O—(CH$_2$—CH$_2$O)$_3$](EtO)$_2$Si(CH$_2$)$_3$—S—C(=O)—R$^4$,
[(C$_{12}$H$_{25}$O—(CH$_2$—CH$_2$O)$_4$](EtO)$_2$Si(CH$_2$)$_3$—S—C(=O)—R$^4$, $[(C_{12}H_{25}O-(CH_2-CH_2O)_5](EtO)_2Si(CH_2)_3-S-C(=O)-R^4,$
$[(C_{12}H_{25}O-(CH_2-CH_2O)_6](EtO)_2Si(CH_2)_3-S-C(=O)-R^4,$
$[(C_{13}H_{27}O-(CH_2-CH_2O)_2](EtO)_2Si(CH_2)_3-S-C(=O)-R^4,$
$[(C_{13}H_{27}O-(CH_2-CH_2O)_3](EtO)_2Si(CH_2)_3-S-C(=O)-R^4,$
$[(C_{13}H_{27}O-(CH_2-CH_2O)_4](EtO)_2Si(CH_2)_3-S-C(=O)-R^4,$
$[(C_{13}H_{27}O-(CH_2-CH_2O)_5](EtO)_2Si(CH_2)_3-S-C(=O)-R^4,$
$[(C_{13}H_{27}O-(CH_2-CH_2O)_6](EtO)_2Si(CH_2)_3-S-C(=O)-R^4,$
$[(C_{14}H_{29}O-(CH_2-CH_2O)_3](EtO)_2Si(CH_2)_3-S-C(=O)-R^4,$
$[(C_{14}H_{29}O-(CH_2-CH_2O)_4](EtO)_2Si(CH_2)_3-S-C(=O)-R^4,$
$[(C_{14}H_{29}O-(CH_2-CH_2O)_5](EtO)_2Si(CH_2)_3-S-C(=O)-R^4,$
$[(C_{14}H_{29}O-(CH_2-CH_2O)_6](EtO)_2Si(CH_2)_3-S-C(=O)-R^4,$
$[(C_{11}H_{23}O-(CH_2-CH_2O)_2]_2(EtO)Si(CH_2)_3-S-C(=O)-R^4,$
$[(C_{11}H_{23}O-(CH_2-CH_2O)_3]_2(EtO)Si(CH_2)_3-S-C(=O)-R^4,$
$[(C_{11}H_{23}O-(CH_2-CH_2O)_4]_2(EtO)Si(CH_2)_3-S-C(=O)-R^4,$
$[(C_{11}H_{23}O-(CH_2-CH_2O)_5]_2(EtO)Si(CH_2)_3-S-C(=O)-R^4,$
$[(C_{11}H_{23}O-(CH_2-CH_2O)_6]_2(EtO)Si(CH_2)_3-S-C(=O)-R^4,$
$[(C_{12}H_{25}O-(CH_2-CH_2O)_2]_2(EtO)Si(CH_2)_3-S-C(=O)-R^4,$
$[(C_{12}H_{25}O-(CH_2-CH_2O)_3]_2(EtO)Si(CH_2)_3-S-C(=O)-R^4,$
$[(C_{12}H_{25}O-(CH_2-CH_2O)_4]_2(EtO)Si(CH_2)_3-S-C(=O)-R^4,$
$[(C_{12}H_{25}O-(CH_2-CH_2O)_5]_2(EtO)Si(CH_2)_3-S-C(=O)-R^4,$
$[(C_{12}H_{25}O-(CH_2-CH_2O)_6]_2(EtO)Si(CH_2)_3-S-C(=O)-R^4,$
$[(C_{13}H_{27}O-(CH_2-CH_2O)_2]_2(EtO)Si(CH_2)_3-S-C(=O)-R^4,$
$[(C_{13}H_{27}O-(CH_2-CH_2O)_3]_2(EtO)Si(CH_2)_3-S-C(=O)-R^4,$
$[(C_{13}H_{27}O-(CH_2-CH_2O)_4]_2(EtO)Si(CH_2)_3-S-C(=O)-R^4,$
$[(C_{13}H_{27}O-(CH_2-CH_2O)_5]_2(EtO)Si(CH_2)_3-S-C(=O)-R^4,$
$[(C_{13}H_{27}O-(CH_2-CH_2O)_6]_2(EtO)Si(CH_2)_3-S-C(=O)-R^4,$
$[(C_{14}H_{29}O-(CH_2-CH_2O)_2]_2(EtO)Si(CH_2)_3-S-C(=O)-R^4,$
$[(C_{14}H_{29}O-(CH_2-CH_2O)_3]_2(EtO)Si(CH_2)_3-S-C(=O)-R^4,$
$[(C_{14}H_{29}O-(CH_2-CH_2O)_4]_2(EtO)Si(CH_2)_3-S-C(=O)-R^4,$
$[(C_{14}H_{29}O-(CH_2-CH_2O)_5]_2(EtO)Si(CH_2)_3-S-C(=O)-R^4,$
$[(C_{14}H_{29}O-(CH_2-CH_2O)_6]_2(EtO)Si(CH_2)_3-S-C(=O)-R^4,$
$[(C_{11}H_{23}O-(CH_2-CH_2O)_2]_3Si(CH_2)_3-S-C(=O)-R^4,$
$[(C_{11}H_{23}O-(CH_2-CH_2O)_3]_3Si(CH_2)_3-S-C(=O)-R^4,$
$[(C_{11}H_{23}O-(CH_2-CH_2O)_4]_3Si(CH_2)_3-S-C(=O)-R^4,$
$[(C_{11}H_{23}O-(CH_2-CH_2O)_5]_3Si(CH_2)_3-S-C(=O)-R^4,$
$[(C_{11}H_{23}O-(CH_2-CH_2O)_6]_3Si(CH_2)_3-S-C(=O)-R^4,$
$[(C_{12}H_{25}O-(CH_2-CH_2O)_2]_3Si(CH_2)_3-S-C(=O)-R^4,$
$[(C_{12}H_{25}O-(CH_2-CH_2O)_3]_3Si(CH_2)_3-S-C(=O)-R^4,$
$[(C_{12}H_{25}O-(CH_2-CH_2O)_4]_3Si(CH_2)_3-S-C(=O)-R^4,$
$[(C_{12}H_{25}O-(CH_2-CH_2O)_5]_3Si(CH_2)_3-S-C(=O)-R^4,$
$[(C_{12}H_{25}O-(CH_2-CH_2O)_6]_3Si(CH_2)_3-S-C(=O)-R^4,$
$[(C_{13}H_{27}O-(CH_2-CH_2O)_2]_3Si(CH_2)_3-S-C(=O)-R^4,$
$[(C_{13}H_{27}O-(CH_2-CH_2O)_3]_3Si(CH_2)_3-S-C(=O)-R^4,$
$[(C_{13}H_{27}O-(CH_2-CH_2O)_4]_3Si(CH_2)_3-S-C(=O)-R^4,$
$[(C_{13}H_{27}O-(CH_2-CH_2O)_5]_3Si(CH_2)_3-S-C(=O)-R^4,$
$[(C_{13}H_{27}O-(CH_2-CH_2O)_6]_3Si(CH_2)_3-S-C(=O)-R^4,$
$[(C_{14}H_{29}O-(CH_2-CH_2O)_2]_3Si(CH_2)_3-S-C(=O)-R^4,$
$[(C_{14}H_{29}O-(CH_2-CH_2O)_3]_3Si(CH_2)_3-S-C(=O)-R^4,$
$[(C_{14}H_{29}O-(CH_2-CH_2O)_4]_3Si(CH_2)_3-S-C(=O)-R^4,$
$[(C_{14}H_{29}O-(CH_2-CH_2O)_5]_3Si(CH_2)_3-S-C(=O)-R^4$
or
$[(C_{14}H_{29}O-(CH_2-CH_2O)_6]_3Si(CH_2)_3-S-C(=O)-R^4,$ wherein the alkyl chains $C_{11}$-$C_{14}$ can be linear or branched.

Examples of compounds of the general formula II include the following:

$(MeO)Me_2Si(CH_2)_3SH,$
$(MeO)_2MeSi(CH_2)_3SH,$
$(EtO)Me_2Si(CH_2)_3SH,$
$(EtO)_2MeSi(CH_2)_3SH,$
$(MeO)_2(HO)Si(CH_2)_3SH,$
$(EtO)_2(HO)Si(CH_2)_3SH,$
$(MeO)_3Si(CH_2)_3SH,$
$(EtO)_3Si(CH_2)_3SH,$
$(MeO)Me_2Si(CH_2)_3SCN,$
$(MeO)_2MeSi(CH_2)_3SCN,$
$(EtO)Me_2Si(CH_2)_3SCN,$
$(EtO)_2MeSi(CH_2)_3SCN,$
$(MeO)_2(HO)Si(CH_2)_3SCN,$
$(EtO)_2(HO)Si(CH_2)_3SCN,$
$(MeO)_3Si(CH_2)_3SCN,$
$(EtO)_3Si(CH_2)_3SCN,$
$(MeO)Me_2Si(CH_2)_3-S-C(=O)-R^4,$
$(MeO)_2MeSi(CH_2)_3-S-C(=O)-R^4,$
$(EtO)Me_2Si(CH_2)_3-S-C(=O)-R^4,$
$(EtO)_2MeSi(CH_2)_3-S-C(=O)-R^4,$
$(MeO)_2(HO)Si(CH_2)_3-S-C(=O)-R^4,$
$(EtO)_2(HO)Si(CH_2)_3-S-C(=O)-R^4,$
$(MeO)_3Si(CH_2)_3-S-C(=O)-R^4,$
$(EtO)_3Si(CH_2)_3-S-C(=O)-R^4,$
$(MeO)Me_2Si-CH_2-CH(CH_3)-CH_2-SH,$
$(MeO)Me_2Si-CH_2-CH(CH_3)-CH_2-SCN,$
$(MeO)Me_2Si-CH_2-CH(CH_3)-CH_2-S-C(=O)-R^4,$
$(EtO)Me_2Si-CH_2-CH(CH_3)-CH_2-SH,$
$(EtO)Me_2Si-CH_2-CH(CH_3)-CH_2-SCN,$
$(EtO)Me_2Si-CH_2-CH(CH_3)-CH_2-S-C(=O)-R^4,$
$(MeO)_2MeSi-CH_2-CH(CH_3)-CH_2-SH,$
$(MeO)_2MeSi-CH_2-CH(CH_3)-CH_2-SCN,$
$(MeO)_2MeSi-CH_2-CH(CH_3)-CH_2-S-C(=O)-R^4,$
$(EtO)_2MeSi-CH_2-CH(CH_3)-CH_2-SH,$
$(EtO)_2MeSi-CH_2-CH(CH_3)-CH_2-SCN,$
$(EtO)_2MeSi-CH_2-CH(CH_3)-CH_2-S-C(=O)-R^4,$
$(MeO)_2(HO)Si-CH_2-CH(CH_3)-CH_2-SH,$
$(MeO)_2(HO)Si-CH_2-CH(CH_3)-CH_2-SCN,$
$(MeO)_2(HO)Si-CH_2-CH(CH_3)-CH_2-S-C(=O)-R^4,$
$(EtO)_2(HO)Si-CH_2-CH(CH_3)-CH_2-SH,$
$(EtO)_2(HO)Si-CH_2-CH(CH_3)-CH_2-SCN,$
$(EtO)_2(HO)Si-CH_2-CH(CH_3)-CH_2-S-C(=O)-R^4,$
$(MeO)_3Si-CH_2-CH(CH_3)-CH_2-SH,$
$(MeO)_3Si-CH_2-CH(CH_3)-CH_2-SCN,$
$(MeO)_3Si-CH_2-CH(CH_3)-CH_2-S-C(=O)-R^4,$
$(EtO)_3Si-CH_2-CH(CH_3)-CH_2-SH,$ $(EtO)_3Si-CH_2-CH(CH_3)-CH_2-SCN$ or
$(EtO)_3Si-CH_2-CH(CH_3)-CH_2-S-C(=O)-R^4$, $R^4$ having the definition given above.

Examples of preferred compounds of the general formula III include the following:

$HO-(CH_2-CH_2O)_2-C_{11}H_{23}$, $HO-(CH_2-CH_2O)_3-C_{11}H_{23}$, $HO-(CH_2-CH_2O)_4-C_{11}H_{23}$, $HO-(CH_2-CH_2O)_5-C_{11}H_{23}$, $HO-(CH_2-CH_2O)_6-C_{11}H_{23}$, $HO-(CH_2-CH_2O)_7-C_{11}H_{23}$,
$HO-(CH(CH_3)-CH_2O)_2-C_{11}H_{23}$, $HO-(CH(CH_3)-CH_2O)_3-C_{11}H_{23}$, $HO-(CH(CH_3)-CH_2O)_4-C_{11}H_{23}$, $HO-(CH(CH_3)-CH_2O)_5-C_{11}H_{23}$, $HO-(CH(CH_3)-CH_2O)_6-C_{11}H_{23}$, $HO-(CH(CH_3)-CH_2O)_7-C_{11}H_{23}$,
$HO-(CH_2-CH_2O)_2-C_{12}H_{25}$, $HO-(CH_2-CH_2O)_3-C_{12}H_{25}$, $HO-(CH_2-CH_2O)_4-C_{12}H_{25}$, $HO-(CH_2-CH_2O)_5-C_{12}H_{25}$, $HO-(CH_2-CH_2O)_6-C_{12}H_{25}$, $HO-(CH_2-CH_2O)_7-C_{12}H_{25}$,
$HO-(CH(CH_3)-CH_2O)_2-C_{12}H_{25}$, $HO-(CH(CH_3)-CH_2O)_3-C_{12}H_{25}$, $HO-(CH(CH_3)-CH_2O)_4-C_{12}H_{25}$, $HO-(CH(CH_3)-CH_2O)_5-C_{12}H_{25}$, $HO-(CH(CH_3)-CH_2O)_6-C_{12}H_{25}$, $HO-(CH(CH_3)-CH_2O)_7-C_{12}H_{25}$,
$HO-(CH_2-CH_2O)_2-C_{13}H_{27}$, $HO-(CH_2-CH_2O)_3-C_{13}H_{27}$, $HO-(CH_2-CH_2O)_4-C_{13}H_{27}$, $HO-(CH_2-CH_2O)_5-C_{13}H_{27}$, $HO-(CH_2-CH_2O)_6-C_{13}H_{27}$, $HO-(CH_2-CH_2O)_7-C_{13}H_{27}$,
$HO-(CH(CH_3)-CH_2O)_2-C_{13}H_{27}$, $HO-(CH(CH_3)-CH_2O)_3-C_{13}H_{27}$, $HO-(CH(CH_3)-CH_2O)_4-C_{13}H_{27}$, $HO-(CH(CH_3)-CH_2O)_5-C_{13}H_{27}$, $HO-(CH(CH_3)-CH_2O)_6-C_{13}H_{27}$, $HO-(CH(CH_3)-CH_2O)_7-C_{13}H_{27}$,
$HO-(CH_2-CH_2O)_2-C_{14}H_{29}$, $HO-(CH_2-CH_2O)_3-C_{14}H_{29}$, $HO-(CH_2-CH_2O)_4-C_{14}H_{29}$, $HO-(CH_2-CH_2O)_5-C_{14}H_{29}$, $HO-(CH_2-CH_2O)_6-C_{14}H_{29}$, $HO-(CH_2-CH_2O)_7-C_{14}H_{29}$,
$HO-(CH(CH_3)-CH_2O)_2-C_{14}H_{29}$, $HO-(CH(CH_3)-CH_2O)_3-C_{14}H_{29}$, $HO-(CH(CH_3)-CH_2O)_4-C_{14}H_{29}$, $HO-(CH(CH_3)-CH_2O)_5-C_{14}H_{29}$, $HO-(CH(CH_3)-CH_2O)_6-C_{14}H_{29}$, $HO-(CH(CH_3)-CH_2O)_7-C_{14}H_{29}$,
$HO-(CH_2-CH_2O)_2-C_{15}H_{31}$, $HO-(CH_2-CH_2O)_3-C_{15}H_{31}$, $HO-(CH_2-CH_2O)_4-C_{15}H_{31}$, $HO-(CH_2-CH_2O)_5-C_{15}H_{31}$, $HO-(CH_2-CH_2O)_6-C_{15}H_{31}$, $HO-(CH_2-CH_2O)_7-C_{15}H_{31}$,
$HO-(CH(CH_3)-CH_2O)_2-C_{15}H_{31}$, $HO-(CH(CH_3)-CH_2O)_3-C_{15}H_{31}$, $HO-(CH(CH_3)-CH_2O)_4-C_{15}H_{31}$, $HO-(CH(CH_3)-CH_2O)_5-C_{15}H_{31}$, $HO-(CH(CH_3)-CH_2O)_6-C_{15}H_{31}$, $HO-(CH(CH_3)-CH_2O)_7-C_{15}H_{31}$,
$HO-(CH_2-CH_2O)_2-C_{16}H_{33}$, $HO-(CH_2-CH_2O)_3-C_{16}H_{33}$, $HO-(CH_2-CH_2O)_4-C_{16}H_{33}$, $HO-(CH_2-CH_2O)_5-C_{16}H_{33}$, $HO-(CH_2-CH_2O)_6-C_{16}H_{33}$, $HO-(CH_2-CH_2O)_7-C_{16}H_{33}$,
$HO-(CH(CH_3)-CH_2O)_2-C_{16}H_{33}$, $HO-(CH(CH_3)-CH_2O)_3-C_{16}H_{33}$, $HO-(CH(CH_3)-CH_2O)_4-C_{16}H_{33}$, $HO-(CH(CH_3)-CH_2O)_5-C_{16}H_{33}$, $HO-(CH(CH_3)-CH_2O)_6-C_{16}H_{33}$, $HO-(CH(CH_3)-CH_2O)_7-C_{16}H_{33}$,
$HO-(CH_2-CH_2O)_2-C_{17}H_{35}$, $HO-(CH_2-CH_2O)_3-C_{17}H_{35}$, $HO-(CH_2-CH_2O)_4-C_{17}H_{35}$, $HO-(CH_2-CH_2O)_5-C_{17}H_{35}$, $HO-(CH_2-CH_2O)_6-CH_{35}$, $HO-(CH_2-CH_2O)_7-C_{17}H_{35}$,
$HO-(CH(CH_3)-CH_2O)_2-C_{17}H_{35}$, $HO-(CH(CH_3)-CH_2O)_3-C_{17}H_{35}$, $HO-(CH(CH_3)-CH_2O)_4-C_{17}H_{35}$, $HO-(CH(CH_3)-CH_2O)_5-C_{17}H_{35}$, $HO-(CH(CH_3)-CH_2O)_6-C_{17}H_{35}$ or $HO-(CH(CH_3)-CH_2O)_7-C_{17}H_{35}$.

The alcohols of the general formula III may have an average branching number of the carbon chain Alk of 1 to 5, preferably 1.2 to 4. The average branching number is defined in this case as the number of $CH_3$ groups -1.

As the catalyst use may be made of metallic compounds, such as metal chlorides, metal oxides, metal oxychlorides, metal alkoxides and metal amides, or transition metal compounds having multiple bonded ligands.

The metallic compounds may for example be halides, oxides, imides, alkoxides, amides, thiolates, carboxylates and/or combinations of these substituents of elements of main groups 3 and 4 of the Periodic Table of the Elements (PTE) and also of transition groups 3, 4, 5, 6 and 7 of the PTE. The metal compounds may have free coordination sites on the metal.

In one particular version, titanates may be used, such as tetra-n-butyl orthotitanate, for example.

As proton-donating co-catalysts, compounds which before and/or during and/or after the transesterification reaction provide protons or react with release of protons, may be used.

Compounds which can be used as proton-donating co-catalysts may more particularly be Brönsted acids. Such acids may be hydrogen compounds of main group 7 of the PTE, and also hydrogen-oxygen compounds of main groups 3, 4, 5, 6 and 7 of the PTE and also of transition groups 4, 5, 6, 7 and 8 of the PTE.

Alternatively, compounds which can be used as proton-donating co-catalysts may be compounds which react with alcohols of the general formula III, with release of protons, before and/or during and/or after the reaction. Such compounds may be, for example, halogen compounds of main groups 3, 4, 5 and 6 and also of transition groups 4, 5, 6, 7 and 8 of the PTE. Moreover, such compounds may be anhydrides of the oxo acids of elements of main groups 3, 4, 5 and 6 and also of transition groups 4, 5, 6, 7 and 8 of the PTE.

The compounds may comprise one or more organic radicals, such as alkyl chains, for example, which may be functionalized with heteroatoms.

Examples of such compounds include carboxylic chlorides or carboxylic anhydrides.

In one particular version, organylchlorosilanes, such as chloromethyltrichloro-silane, chloropropyltrichlorosilane or chloropropyldiethoxychlorosilane, for example, may be used.

Moreover, solid-phase-bound protons as proton-donating co-catalysts may be used. Examples of sources of such protons include acidic ion-exchange resins, such as Amberlyst 15, Dowex 50 or Deloxan ASP I/9.

These proton-donating co-catalysts may be added before and/or during and/or after the reaction.

The weight ratio of catalyst to proton-donating co-catalyst may be preferably 1:1 to 0:1, more preferably 0.5:1 to 0:1.

In one particular embodiment, when using the abovementioned proton-donating co-catalysts, to do wholly or partly without the use of the stated catalysts.

Moreover, the alkylpolyether-substituted mercaptosilanes of the general formula I may be treated with the proton-donating co-catalysts, for the purpose of decoloring, only after the silanes have been prepared.

Excess protons can be destroyed and/or separated off during and/or after the reaction.

The reaction may be carried out at temperatures between 20 and 200° C., preferably between 50 and 170° C., more preferably between 80 and 150° C. In order to avoid condensation reactions it may be advantageous to carry out the reaction in a water-free environment, ideally in an inert gas atmosphere.

The reaction can be carried out under atmospheric pressure or reduced pressure. The reaction may be carried out continuously or batchwise.

The invention further provides rubber mixtures comprising the alkylpolyether-substituted mercaptosilanes of the general formula I of the invention, with a Hazen colour number of ≦250 mg Pt—Co/L, preferably ≦200 mg Pt—Co/L.

The process of the invention has the advantage that alkylpolyether-substituted mercaptosilanes having a Hazen colour number ≦250 mg Pt—Co/L can be prepared.

This preparation may take place in one step; after treatment of the compounds obtained is not necessarily required. The proton-donating co-catalysts described, moreover, may wholly or partly replace the catalysts used to date.

EXAMPLES

The following examples further describe and demonstrate embodiments of the present invention. The examples are given solely for the purposes of illustration and are not to be construed as limitations of the present invention.

The ethoxylated isotridecanols used are sales products of the companies BASF (Lutensol TO 5) and Sasol (Marlipal O13/50) and have an average degree of ethoxylation of approximately 5. Titanium tetrabutoxide and acetic anhydride can be obtained from Merck and used without further purification. Chloromethyltri-chlorosilane, chloropropyltrichlorosilane and Amberlyst 15 dry (a sulphonic acid-functionalized styrene-divinylbenzene copolymer) can be obtained from Sigma-Aldrich and used without further purification.

3-Mercaptopropyltriethoxysilane (MPTES) is a product of Degussa GmbH and can be obtained under the trade name VP Si 263.

The product can be characterized by mass spectrometry and NMR spectroscopy.

The Hazen colour number is determined in accordance with DIN/ISO 6271.

Example 1

Comparative Example to Examples 2-5

A 500 ml flask with distillation bridge is charged under $N_2$ inert gas with 88.5 g of Lutensol TO 5 (0.21 mol) and 88.5 g of Marlipal O13/50 (0.21 mol) and also 25 μL of Ti(On-Bu)$_4$. 50 g of MPTES (0.21 mol) are added. Then the mixture is heated at 140° C. for 1 h, after which time the pressure is lowered to 20 mbar. The end of the reaction is determined by the amount of ethanol distilled off. The result is an orange-brown, slightly turbid liquid with a yield of 98%.

Hazen colour number: 360 mg Pt—Co/L

Example 2

A 500 ml flask with distillation bridge is charged under $N_2$ inert gas with 88.5 g of Lutensol TO 5 (0.21 mol) and 88.5 g of Marlipal O13/50 (0.21 mol) and also 25 μL of Ti(On-Bu)$_4$ and 137 μL of chloromethyltrichlorosilane. 50 g of MPTES (0.21 mol) are added. Then the mixture is heated at 140° C. for 1 h, after which time the pressure is lowered to approximately 20 mbar. The end of the reaction is determined by the amount of ethanol distilled off. The result is a pale grey, slightly turbid liquid with a quantitative yield.

Hazen colour number: 150 mg Pt—Co/L

Example 3

A 500 ml flask with distillation bridge is charged under $N_2$ inert gas with 35.2 g of Lutensol TO 5 (0.08 mol) and 35.2 g of Marlipal O13/50 (0.08 mol) and also 10 μL of Ti(On-Bu)$_4$ and 55 μL of chloropropyltrichlorosilane. 20 g of MPTES (0.08 mol) are added. Then the mixture is heated at 140° C. for 1 h, after which time the pressure is lowered to 20 mbar. The end of the reaction is determined by the amount of ethanol distilled off. The result is a pastel-violet liquid with a yield of 99%.

Hazen colour number: 170 mg Pt—Co/L

Example 4

A 500 ml flask with distillation bridge is charged under $N_2$ inert gas with 88.5 g of Lutensol TO 5 (0.21 mol) and 88.5 g of Marlipal O13/50 (0.21 mol) and also 25 μL of Ti(On-Bu)$_4$ and 500 mg of acetic anhydride. 50 g of MPTES (0.21 mol) are added. Then the mixture is heated at 140° C. for 1 h, after which time the pressure is lowered to 20 mbar. The end of the reaction is determined by the amount of ethanol distilled off. The result is a beige-red liquid with a quantitative yield.

Hazen colour number: 140 mg Pt—Co/L

Example 5

A 500 ml flask with distillation bridge is charged under $N_2$ inert gas with 35.2 g of Lutensol TO 5 (0.08 mol) and 35.2 g of Marlipal O13/50 (0.08 mol) and also 12.6 μL of Ti(On-Bu)$_4$ and 1 g of Amberlyst 15 dry. 20 g of MPTES (0.08 mol) are added. Then the mixture is heated at 140° C. for 1 h, after which time the pressure is lowered to 20 mbar. The end of the reaction is determined by the amount of ethanol distilled off. The result is an old-rose-coloured liquid with a quantitative yield.

Hazen colour number: 160 mg Pt—Co/L

Example 6

Comparative Example to Examples 7 and 8

A 500 ml flask with distillation bridge is charged under $N_2$ inert gas with 75.6 g of Lutensol TO 5 (0.18 mol) and 75.6 g of Marlipal O13/50 (0.18 mol) and also 21.4 μL of Ti(On-Bu)$_4$. 42.8 g of MPTES (0.18 mol) are added. Then the mixture is heated at 140° C. for 1 h, after which time the pressure is lowered to 30 mbar. The end of the reaction is determined by the amount of ethanol distilled off. The result is a dark-red, slightly turbid liquid with a yield of 92%.

Hazen colour number: >1000 mg Pt—Co/L

Example 7

A 500 ml flask with distillation bridge is charged under $N_2$ inert gas with 35.2 g of Lutensol TO 5 (0.08 mol) and 35.2 g of Marlipal O13/50 (0.08 mol) and also 12.6 μL of Ti(On-Bu)$_4$ and 119 μL of chloromethyltrichlorosilane. 20.1 g of MPTES (0.08 mol) are added. Then the mixture is heated at 140° C. for 1 h, after which time the pressure is lowered to 20 mbar. The end of the reaction is determined by the amount of ethanol distilled off. The result is a pale-yellow, clear liquid with a yield of 99%.

Hazen colour number: 55 mg Pt—Co/L

Example 8

A 500 ml flask with distillation bridge is charged under $N_2$ inert gas with 35.6 g of Lutensol TO 5 (0.08 mol) and 35.6 g of Marlipal O13/50 (0.08 mol) and also 1.02 g of Amberlyst 15 dry ion-exchange resin. 20.2 g of MPTES (0.08 mol) are added. Then the mixture is heated at 140° C. for 1 h, after which time the pressure is lowered to 20 mbar. The end of the reaction is determined by the amount of ethanol distilled off. The result is a pale-yellow, clear liquid with a yield of 98%.

Hazen colour number: 140 mg Pt—Co/L

Example 9

Comparative Example to Example 10

A 500 ml flask with distillation bridge is charged under $N_2$ inert gas with 50 g of Lutensol TO 5 (0.12 mol) and 50 g of Marlipal O13/50 (0.12 mol) and also 14 μL of Ti(On-Bu)$_4$. 28 g of MPTES (0.12 mol) are added. Then the mixture is heated at 140° C. for 1 h, after which time the pressure is lowered to 20 mbar. The end of the reaction is determined by the amount of ethanol distilled off. The result is an orange-brown liquid with a quantitative yield.

Hazen colour number: 330 mg Pt—Co/L

Example 10

A 500 ml flask with distillation bridge is charged under $N_2$ inert gas with 70.5 g of Lutensol TO 5 (0.17 mol) and 70.5 g of Marlipal O13/50 (0.17 mol) and also 238 μL of chloromethyltrichlorosilane. 40 g of MPTES (0.17 mol) are added. Then the mixture is heated at 140° C. for 1 h, after which time the pressure is lowered to 20 mbar. The end of the reaction is determined by the amount of ethanol distilled off. The result is a beige-red liquid with a quantitative yield.

Hazen colour number: 30 mg Pt—Co/L

Example 11

In a round-bottomed flask, 50 g of the Degussa silane VP Si 363 (colour number: 480 mg of Pt—Co/L) are treated with 5 g of Amberlyst 15 dry ion-exchange resin at 50° C. for 30 minutes. Subsequently the ion-exchanger is separated off.

Hazen colour number: after separation, 190 mg Pt—Co/L

The description in German priority application DE 102007037556.7, filed Aug. 9, 2007, is incorporated by reference herein.

The invention claimed is:

1. A process for preparing alkylpolyether-substituted mercaptosilanes of the general formula I, $$(X)_m(X')_n(X'')_oSi(-R^1-SR^2)_p \quad (I)$$

wherein p is 1, 2 or 3, m is 1, 2 or 3, n and o are 0, 1 or 2, and m+p+n+o is 4, the groups X are the same or different and X is an alkylpolyether group
O—((CR$^3_2$)$_w$—O—)$_v$Alk, where
v=1-40,
w=1-40,
R$^3$ independently at each occurrence is H, a phenyl group or an unbranched or branched alkyl group,
Alk is a branched or unbranched, saturated or unsaturated, substituted or unsubstituted, aliphatic, aromatic or mixed aliphatic/aromatic monovalent C$_1$-C$_{35}$ hydrocarbon group,
the groups X' are the same or different and X' is a branched or unbranched alkoxy group,
a branched or unbranched C$_2$-C$_{25}$ alkenyloxy group,
a C$_6$-C$_{35}$ aryloxy group,
a branched or unbranched C$_7$-C$_{35}$ alkylaryloxy group,
a branched or unbranched C$_7$-C$_{35}$ aralkyloxy group,
or a hydroxyl group (—OH), the groups X" are the same or different and X" independently at each occurance is a branched or unbranched alkyl group,
R$^1$ is a branched or unbranched, saturated or unsaturated, aliphatic, aromatic or mixed aliphatic/aromatic divalent C$_1$-C$_{30}$ hydrocarbon group which is unsubstituted or substituted by heteroatoms,
R$^2$ is CN, H or —C(Het)-Alk, where Het is a doubly bonded heteroatom O, S or NAlk and Alk has the definition given above, having a Hazen colour number of ≦250 mg Pt—Co/L, comprising reacting compounds of the general formula II, $$(X')_{m+n}(X'')_oSi(-R^1-SR^2)_p \quad (II)$$

wherein X', X", R$^1$, R$^2$, m, n, o and p have the definitions given above, with m equivalents of the compounds of the general formula III, $$H-O-((CR^3_2)_w-O-)_vAlk \quad (III)$$

wherein R$^3$, Alk, v and w have the definitions given above, in the presence of a proton-donating co-catalyst and a catalyst, and
separating off liberated X'—H from the reaction mixture; wherein the proton-donating co-catalyst comprises an acidic ion exchange resin.

2. The process according to claim 1, wherein the proton-donating co-catalyst is added beforehand and/or during the reaction.

3. The process according to claim 1, wherein the proton-donating co-catalyst comprises a compound which before and/or during the reaction provides protons or reacts with release of protons.

4. The process according to claim 1, wherein the proton-donating co-catalyst comprises a Brönsted acid.

5. The process according to claim 1, wherein the reaction is carried out at 20-200° C.

6. The process according to claim 1, wherein the reaction is carried out in a water-free inert gas atmosphere.

7. The process according to claim 1, wherein the Hazen colour number of ≦200 mg Pt—Co/L.

8. The process according to claim 1, wherein
p is 1,
X is O—(CH$_2$—CH$_2$—O—)$_v$Alk or O—(CH(CH$_3$)—CH$_2$—O—)$_v$Alk, v=5-16, w=2-10, Alk is a C$_6$-C$_{10}$ hydrocarbon group,
X' is selected from the group consisting of
—OCH$_3$, —OCH$_2$—CH$_3$, —OCH(CH$_3$)—CH$_3$, —OCH$_2$—CH$_2$—CH$_3$, —OC$_{12}$H$_{25}$, —OC$_{13}$H$_{27}$, —OC$_{14}$H$_{29}$, C$_{15}$-C$_{18}$ alkoxy, C$_6$ to C$_{18}$ alkenyloxy; —OC$_6$H$_5$, C$_9$-C$_{18}$ aryloxy;
—O—CH$_2$—C$_6$H$_5$, —O—CH$_2$—CH$_2$—C$_6$H$_5$, —O—C$_6$H$_4$—CH$_3$, C$_9$-C$_{18}$ aralkyloxy group, and
—OH, and
X" is CH$_3$, CH$_2$—CH$_3$, CH(CH$_3$)—CH$_3$, CH$_2$—CH$_2$—CH$_3$ or C$_4$-C$_{18}$ alkyl group.

9. A process for preparing alkylpolyether-substituted mercaptosilanes of the general formula I, $$(X)_m(X')_n(X'')_oSi(-R^1-SR^2)_p \quad (I)$$

wherein p is 1, 2 or 3, m is 1, 2 or 3, n and o are 0, 1 or 2, and m+p+n+o is 4,
the groups X are alike or different and X is an alkylpolyether group
O—((CR$^3_2$)$_w$—O—)$_v$Alk, where
v=1-40,
w=1-40, $R^3$ independently at each occurrence is H, a phenyl group or an unbranched or branched alkyl group, Alk is a branched or unbranched, saturated or unsaturated, substituted or unsubstituted, aliphatic, aromatic or mixed aliphatic/aromatic monovalent $C_1$-$C_{35}$ hydrocarbon group, the groups X' are the same or different and X' is a branched or unbranched alkoxy group, a branched or unbranched $C_2$-$C_{25}$ alkenyloxy group, a $C_6$-$C_{35}$ aryloxy group, a branched or unbranched $C_7$-$C_{35}$ alkylaryloxy group, a branched or unbranched $C_7$-$C_{35}$ aralkyloxy group, or a hydroxyl group (—OH), the groups X" are the same or different and X" independently at each occurrence is a branched or unbranched alkyl group, $R^1$ is a branched or unbranched, saturated or unsaturated, aliphatic, aromatic or mixed aliphatic/aromatic divalent $C_1$-$C_{30}$ hydrocarbon group which is unsubstituted or substituted by heteroatoms, $R^2$ is CN, H or —C(Het)-Alk, wherein Het is a doubly bonded heteroatom O, S or NAlk and Alk has the definition given above, having a Hazen colour number of $\leq$250 mg Pt13 Co/L, comprising reacting compounds of the general formula II,

wherein X', X", $R^1$, $R^2$, m, n, o and p have the definitions given above, with m equivalents of the compounds of the general formula III,

wherein $R^3$, Alk, v and w have the definitions given above, in the presence of a proton-donating co-catalyst and a catalyst, and separating off liberated X'—H from the reaction mixture;

wherein the proton-donating co-catalyst comprises an organylchlorosilane.

10. The process according to claim 9, wherein the organylchlorosilane is chloromethyltrichlorosilane, chloropropyltrichlorosilane or chloropropyldiethoxychlorosilane.

* * * * *